United States Patent
Guerra Filho et al.

(10) Patent No.: US 12,141,937 B1
(45) Date of Patent: Nov. 12, 2024

(54) FITNESS SYSTEM

(71) Applicant: Apple Inc., Cupertino, CA (US)

(72) Inventors: Gutemberg B. Guerra Filho, El Dorado Hills, CA (US); Saumil B. Patel, San Jose, CA (US)

(73) Assignee: Apple Inc., Cupertino, CA (US)

( * ) Notice: Subject to any disclaimer, the term of this patent is extended or adjusted under 35 U.S.C. 154(b) by 489 days.

(21) Appl. No.: 16/862,375

(22) Filed: Apr. 29, 2020

Related U.S. Application Data

(60) Provisional application No. 62/852,515, filed on May 24, 2019.

(51) Int. Cl.
  *G06T 3/10* (2024.01)
  *A61B 5/107* (2006.01)
  *G06T 3/18* (2024.01)
  *G06T 7/33* (2017.01)

(52) U.S. Cl.
  CPC .............. *G06T 3/10* (2024.01); *A61B 5/1079* (2013.01); *G06T 3/18* (2024.01); *G06T 7/337* (2017.01); *A63B 2220/05* (2013.01)

(58) Field of Classification Search
  CPC ..... G06T 3/0056; G06T 7/337; G06T 3/0093; A61B 5/1079; A63B 2220/05
  USPC ......... 382/276, 103; 482/8; 434/257; 396/14
  See application file for complete search history.

(56) References Cited

U.S. PATENT DOCUMENTS

| | | | | |
|---|---|---|---|---|
| 6,643,385 B1* | 11/2003 | Bravomalo | ............. | G06T 11/00 |
| | | | | 345/646 |
| 7,298,881 B2* | 11/2007 | Giger | .................... | G06T 7/0012 |
| | | | | 600/407 |
| 7,925,887 B2* | 4/2011 | Burton | .................... | G16H 30/20 |
| | | | | 340/5.82 |
| 8,103,090 B2* | 1/2012 | Ma | ........................ | G06V 10/764 |
| | | | | 348/169 |
| 10,321,728 B1* | 6/2019 | Koh | .......................... | G06T 7/11 |
| 10,509,952 B2* | 12/2019 | Kastaniotis | .......... | G06V 40/172 |
| 2004/0131227 A1* | 7/2004 | Bravomalo | ........ | G06Q 30/0269 |
| | | | | 382/100 |
| 2007/0179816 A1* | 8/2007 | Lemme | .................. | G16H 20/30 |
| | | | | 482/8 |
| 2007/0274574 A1* | 11/2007 | Boult | .................... | G06V 40/107 |
| | | | | 382/119 |
| 2010/0111370 A1* | 5/2010 | Black | .................. | G06F 18/2321 |
| | | | | 705/26.1 |
| 2010/0290668 A1* | 11/2010 | Friedman | ............... | G06V 40/19 |
| | | | | 348/78 |
| 2012/0045117 A1* | 2/2012 | Li | ............................ | G06T 7/77 |
| | | | | 382/154 |
| 2012/0165703 A1* | 6/2012 | Bottum | .................. | G16H 20/30 |
| | | | | 600/595 |

(Continued)

*Primary Examiner* — Kathleen Y Dulaney
(74) *Attorney, Agent, or Firm* — Fernando & Partners, LLP

(57) ABSTRACT

A method includes obtaining one or more images associated with a user. The method further includes generating, using a body-assessment classifier, one or more body-assessment vectors. Each of the one or more body-assessment vectors is a function of a particular one of the one or more images. The one or more body-assessment vectors include quantitative physique and biometric assessments associated with the user. The method further includes displaying, on the display, a body-assessment indicator that is based on the one or more body-assessment vectors.

19 Claims, 20 Drawing Sheets

(56) References Cited

U.S. PATENT DOCUMENTS

| | | | |
|---|---|---|---|
| 2013/0121529 A1* | 5/2013 | Fleisher | G01S 7/412 |
| | | | 382/103 |
| 2014/0219520 A1* | 8/2014 | Myers | G06V 40/1365 |
| | | | 382/124 |
| 2014/0226900 A1* | 8/2014 | Saban | H04N 23/63 |
| | | | 382/165 |
| 2014/0254883 A1* | 9/2014 | Kim | G06V 10/764 |
| | | | 382/107 |
| 2014/0286533 A1* | 9/2014 | Luo | G06V 40/18 |
| | | | 382/103 |
| 2015/0037771 A1* | 2/2015 | Kaleal, III | G16H 20/30 |
| | | | 434/257 |
| 2015/0038806 A1* | 2/2015 | Kaleal, III | A61B 5/4833 |
| | | | 600/301 |
| 2015/0294189 A1* | 10/2015 | Benhimane | G06F 18/28 |
| | | | 382/195 |
| 2015/0334065 A1* | 11/2015 | Yan | H04L 51/52 |
| | | | 709/206 |
| 2016/0012646 A1* | 1/2016 | Huang | G06T 19/20 |
| | | | 345/419 |
| 2016/0088284 A1* | 3/2016 | Sareen | G06T 3/60 |
| | | | 348/47 |
| 2016/0220867 A1* | 8/2016 | Flaherty | G16H 20/40 |
| 2017/0087415 A1* | 3/2017 | Nandimandalam | |
| | | | G09B 19/0092 |
| 2017/0273639 A1* | 9/2017 | Iscoe | G06N 20/00 |
| 2017/0344808 A1* | 11/2017 | El-Khamy | G06V 40/161 |
| 2019/0066493 A1* | 2/2019 | Sohn | G06N 3/08 |
| 2019/0197755 A1* | 6/2019 | Vats | G06T 13/40 |
| 2019/0205643 A1* | 7/2019 | Liu | G06N 3/045 |
| 2020/0160544 A1* | 5/2020 | Yao | G06V 10/225 |

\* cited by examiner

300

400

Body-Assessment Vector
410-1

| First Image 420-1 | Gender Value 430a-1 | Bodyfat Value 430b-1 | Weight Value 430c-1 | ... | Sub-Value No. 430N-1 |

Body-Assessment Vector
410-2

| Second Image 420-2 | Gender Value 430a-2 | Bodyfat Value 430b-2 | Weight Value 430c-2 | ... | Sub-Value No. 430N-2 |

Body-Assessment Vector
410-3

| Third Image 420-3 | Gender Value 430a-3 | Bodyfat Value 430b-3 | Weight Value 430c-3 | ... | Sub-Value No. 430N-3 |

●
●
●

Body-Assessment Vector
410-M

| $M^{th}$ Image 420-M | Gender Value 430a-M | Bodyfat Value 430b-M | Weight Value 430c-M | ... | Sub-Value No. 430N-M |

Figure 4

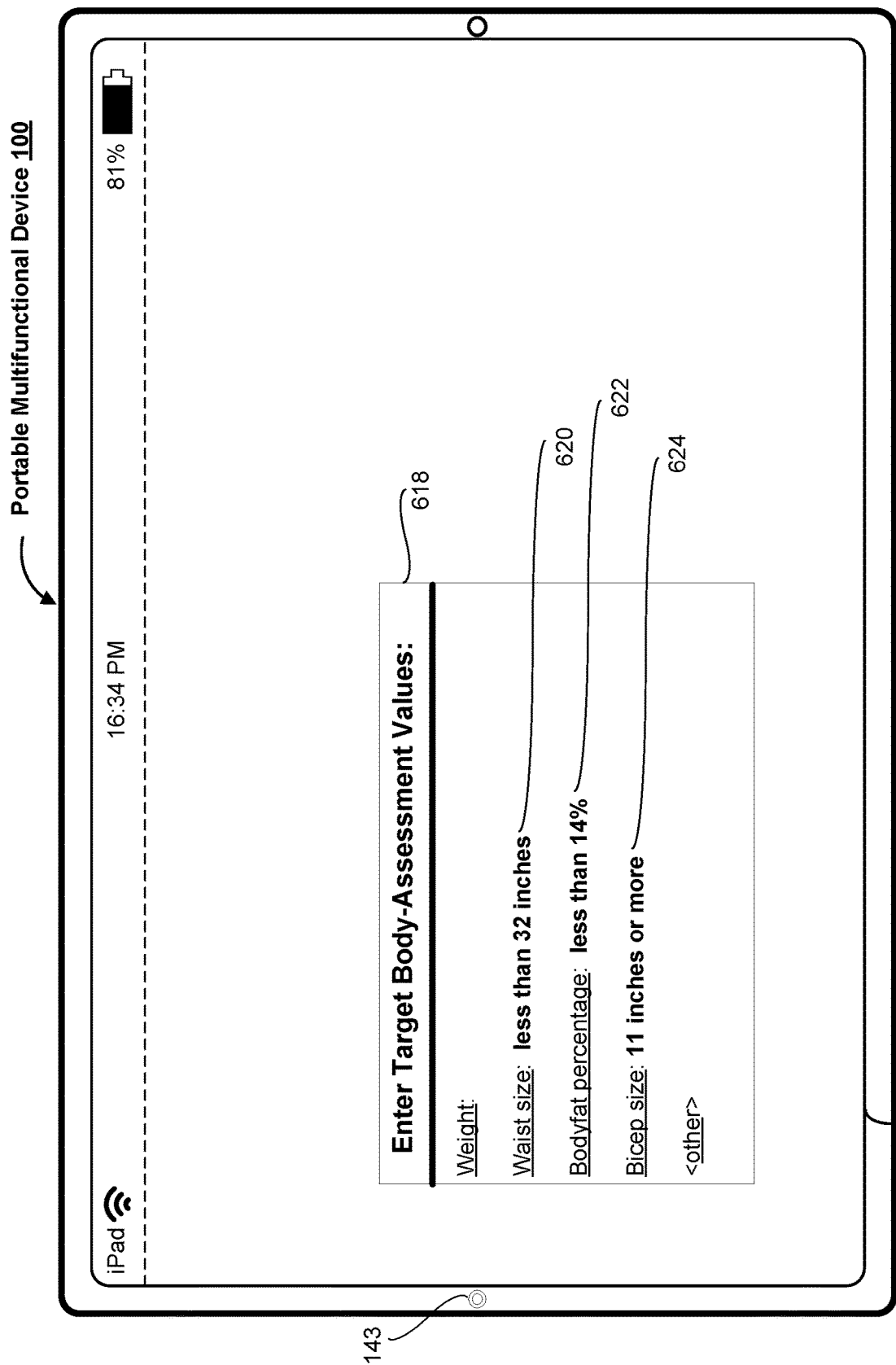

FITNESS SYSTEM

CROSS-REFERENCE TO RELATED APPLICATION

This application claims priority to U.S. Provisional Patent App. No. 62/852,515, filed on May 24, 2019, which is hereby incorporated by reference in its entirety.

TECHNICAL FIELD

The present disclosure relates to a fitness system, and, in particular, assessing body composition based on visual information.

BACKGROUND

Users, without the aid of specialized medical equipment (e.g., weight scale, body fat calipers), are limited to taking before and after images of their bodies in order to assess the effects of a fitness program. The assessments are merely qualitative. However, a user is unable to ascertain quantitative physique and biometric assessments of his or her body from the images alone. As a result, the user does not have a way to quantitatively track physique and biometric changes resulting from the user following a fitness program. Moreover, based on the images alone, a current system cannot generate a visual indication of the body of the user that is based on the quantitative physique and biometric assessments of the user.

SUMMARY

In accordance with some implementations, a method is performed at an electronic device with one or more processors and a non-transitory memory. The method includes obtaining a training data corpus that includes a plurality of image data sets. Each of the plurality of image data sets is associated with a respective individual. Each of the plurality of image data sets is associated with respective one or more body-assessment indicator values. The one or more body-assessment indicator values are visually assessable. The method further includes generating, using a body-assessment classifier, at least one candidate body-assessment indicator value corresponding to a portion of the plurality of image data sets. The method further includes comparing the at least one candidate body-assessment indicator value against a corresponding body-assessment indicator value within the training data corpus. The method further includes in response to determining that a result of the comparison between the at least one candidate body-assessment indicator value against the corresponding body-assessment indicator value does not satisfy an error metric, changing an operational value of the body-assessment classifier. The method further includes in response to determining that the result of the comparison between the at least one candidate body-assessment indicator value against the corresponding body-assessment indicator value satisfies the error metric and that a sufficient portion of the training data corpus is utilized, outputting a convergence indicator associated with the body-assessment classifier.

In accordance with some implementations, a method is performed at an electronic device with one or more processors, a display, and a non-transitory memory. The method includes obtaining one or more images associated with a user. The method further includes generating, using a body-assessment classifier, one or more body-assessment vectors. Each of the one or more body-assessment vectors is a function of a particular one of the one or more images. The one or more body-assessment vectors include quantitative physique and biometric assessments associated with the user. The method further includes displaying, on the display, a body-assessment indicator that is based on the one or more body-assessment vectors.

In accordance with some implementations, an electronic device includes (optionally) a display, one or more processors, non-transitory memory, and one or more programs; the one or more programs are stored in the non-transitory memory and configured to be executed by the one or more processors and the one or more programs include instructions for performing or causing performance of the operations of any of the methods described herein. In accordance with some implementations, a non-transitory computer readable storage medium has stored therein instructions, which, when executed by one or more processors of an electronic device and (optionally) a display, cause the electronic device to perform or cause performance of the operations of any of the methods described herein. In accordance with some implementations, an electronic device includes: (optionally) a display and a means for performing or causing performance of the operations of any of the methods described herein. In accordance with some implementations, an information processing apparatus, for use in an electronic device, includes means for performing or causing performance of the operations of any of the methods described herein.

BRIEF DESCRIPTION OF THE DRAWINGS

For a better understanding of the various described implementations, reference should be made to the Description, below, in conjunction with the following drawings in which like reference numerals refer to corresponding parts throughout the figures.

FIG. 4 is an example of a representation of body-assessment vectors according to some implementations.

FIGS. 6A-6L are examples of a user interface for a fitness system in accordance with some implementations.

SUMMARY

Figure 1:
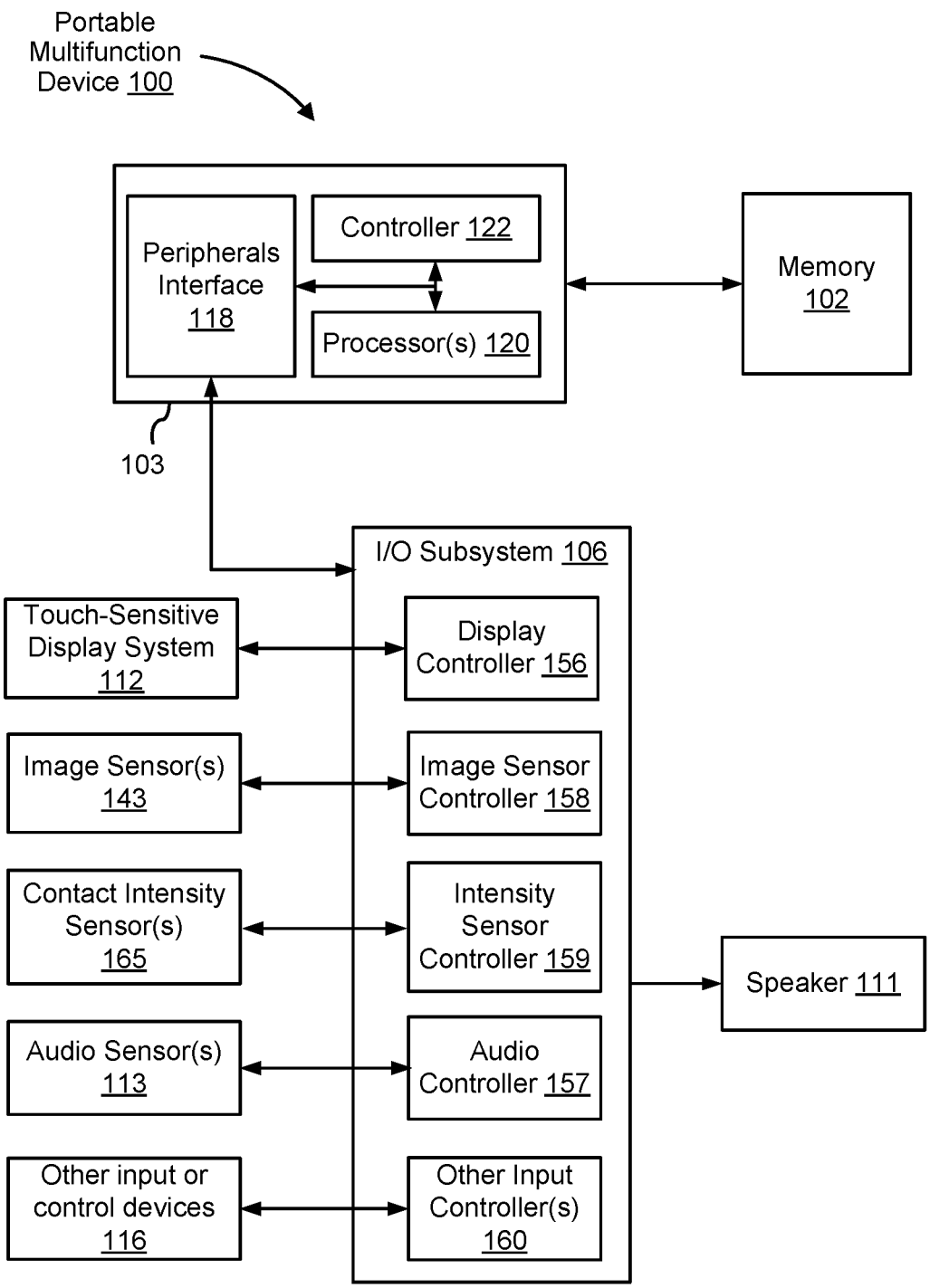
FIG. 1 is a block diagram of an example of a portable multifunction device in accordance with some implementations.

Various implementations provide for training a body-assessment classifier based on a training data corpus that includes a plurality of image data sets corresponding to a plurality of individuals. Each of the plurality of image data sets is associated with one or more body-assessment indicator values. The body-assessment classifier is trained based on a comparison between a candidate body-assessment indicator value generated by the body-assessment classifier against a corresponding body-assessment indicator value. In some implementations, each of the plurality of image data sets includes or is associated with annotation data. In some implementations, the training data corpus includes a plurality of previously unannotated image data sets that were preprocessed in order to generate a corresponding plurality of annotation values.

Moreover, in various implementations, a fitness system utilizes a trained body-assessment classifier in order to generate quantitative physique and biometric assessments of a user, such as the user's weight, height, bodyfat percentage, muscle size, etc. Based on the quantitative physique and biometric assessments of the user, the fitness system may generate one or more visual representations of the user (e.g., model of the user's body). For example, in some implementations, the visual representation of the user corresponds to predicted (e.g., projected) representations of the user were the user to participate in a particular fitness program (e.g., an exercise regime and/or diet regime). For instance, the predicted representations of the user correspond to predicted three-dimensional (3D) models of the user at various stages of the fitness program. As another example, in some implementations, the visual representation of the user corresponds to a target (e.g., goal) visual representation of the user.

DESCRIPTION

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described implementations. The first contact and the second contact are both contacts, but they are not the same contact, unless the context clearly indicates otherwise.

The terminology used in the description of the various described implementations herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including." "comprises," and/or "comprising." when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting." depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 is a block diagram of an example of a portable multifunction device 100 (sometimes hereinafter referred to as an "electronic device" for the sake of brevity) in accordance with some implementations. The electronic device 100 includes memory 102 (which optionally includes one or more computer readable storage mediums), a memory controller 122, one or more central processing units (CPUs) 120, a peripherals interface 118, an input/output (I/O) subsystem 106, a speaker 111, a touch-sensitive display system 112, image sensor(s) 143 (e.g., smartphone camera, HMD camera), contact intensity sensor(s) 165, audio sensor(s) 113 (e.g., microphone), and other input or control device(s) 116.

In some implementations, the peripherals interface 118, the one or more CPUs 120, and the memory controller 122 are, optionally, implemented on a single chip, such as a chip 103. In some implementations, they are implemented on separate chips.

The I/O subsystem 106 couples input/output peripherals on the electronic device 100, such as the touch-sensitive display system 112 and the other input or control devices 116, with the peripherals interface 118. The I/O subsystem 106 optionally includes a display controller 156, an image sensor controller 158, an intensity sensor controller 159, an audio controller 157, and one or more input controllers 160 for other input or control devices. The one or more input controllers 160 receive/send electrical signals from/to the other input or control devices 116. The other input or control devices 116 optionally include physical buttons (e.g., push buttons, rocker buttons, etc.), dials, slider switches, joysticks, click wheels, and so forth. In some alternate implementations, the one or more input controllers 160 are, optionally, coupled with any (or none) of the following: a key board, infrared port, USB port, stylus, and/or a pointer device such as a mouse. The one or more buttons optionally include an up/down button for volume control of the speaker 111 and/or audio sensor(s) 113. The one or more buttons optionally include a push button.

The touch-sensitive display system 112 provides an input interface and an output interface between the electronic device 100 and a user. The display controller 156 receives and/or sends electrical signals from/to the touch-sensitive display system 112. The touch-sensitive display system 112 displays visual output to the user. The visual output optionally includes graphics, text, icons, video, and any combination thereof (collectively termed "graphics"). In some implementations, some or all of the visual output corresponds to user interface objects. As used herein, the term "affordance" refers to a user-interactive graphical user interface object (e.g., a graphical user interface object that is configured to respond to inputs directed toward the graphical user interface object). Examples of user-interactive graphical user interface objects include, without limitation, a button, slider, icon, selectable menu item, switch, hyperlink, or other user interface control.

The touch-sensitive display system 112 has a touch-sensitive surface, sensor, or set of sensors that accepts input from the user based on haptic and/or tactile contact. The touch-sensitive display system 112 and the display controller 156 (along with any associated modules and/or sets of instructions in the memory 102) detect contact (and any movement or breaking of the contact) on the touch-sensitive display system 112 and converts the detected contact into interaction with user-interface objects (e.g., one or more soft keys, icons, web pages or images) that are displayed on the touch-sensitive display system 112. In an example implementation, a point of contact between the touch-sensitive display system 112 and the user corresponds to a finger of the user or a stylus.

The touch-sensitive display system 112 optionally uses LCD (liquid crystal display) technology, LPD (light emitting polymer display) technology, or LED (light emitting diode) technology, although other display technologies are used in other implementations. The touch-sensitive display system 112 and the display controller 156 optionally detect contact and any movement or breaking thereof using any of a plurality of touch-sensing technologies now known or later developed, including but not limited to capacitive, resistive, infrared, and surface acoustic wave technologies, as well as other proximity sensor arrays or other elements for determining one or more points of contact with the touch-sensitive display system 112.

The touch-sensitive display system 112 optionally has a video resolution in excess of 100 dpi. In some implementations, the touch screen video resolution is in excess of 400 dpi (e.g., 500 dpi, 800 dpi, or greater). The user optionally makes contact with the touch-sensitive display system 112 using any suitable object or appendage, such as a stylus, a finger, and so forth. In some implementations, the user interface is designed to work with finger-based contacts and gestures, which can be less precise than stylus-based input due to the larger area of contact of a finger on the touch screen. In some implementations, the electronic device 100 translates the rough finger-based input into a precise pointer/cursor position or command for performing the actions desired by the user.

The speaker 111 and the audio sensor(s) 113 provide an audio interface between a user and the electronic device 100. Audio circuitry receives audio data from the peripherals interface 118, converts the audio data to an electrical signal, and transmits the electrical signal to the speaker 111. The speaker 111 converts the electrical signal to human-audible sound waves. Audio circuitry also receives electrical signals converted by the audio sensors 113 (e.g., a microphone) from sound waves. Audio circuitry converts the electrical signal to audio data and transmits the audio data to the peripherals interface 118 for processing. Audio data is, optionally, retrieved from and/or transmitted to the memory 102 and/or RF circuitry by the peripherals interface 118. In some implementations, audio circuitry also includes a headset jack. The headset jack provides an interface between audio circuitry and removable audio input/output peripherals, such as output-only headphones or a headset with both output (e.g., a headphone for one or both ears) and input (e.g., a microphone).

The image sensor(s) 143 capture still images and/or video. In some implementations, an image sensor 143 is located on the back of the electronic device 100, opposite a touch screen on the front of the electronic device 100, so that the touch screen is enabled for use as a viewfinder for still and/or video image acquisition. In some implementations, another image sensor 143 is located on the front of the electronic device 100 so that the user's image(s) are obtained. In some implementations, the image sensor(s) corresponds to a camera integrated within a head-mounted display (HMD).

The contact intensity sensors 165 detect intensity of contacts on the electronic device 100 (e.g., a touch input on a touch-sensitive surface of the electronic device 100). The contact intensity sensors 165 are coupled with the intensity sensor controller 159 in the I/O subsystem 106. The contact intensity sensor(s) 165 optionally include one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). The contact intensity sensor(s) 165 receive contact intensity information (e.g., pressure information or a proxy for pressure information) from the environment. In some implementations, at least one contact intensity sensor 165 is collocated with, or proximate to, a touch-sensitive surface of the electronic device 100. In some implementations, at least one contact intensity sensor 165 is located on the back of the electronic device 100.

Figure 2:
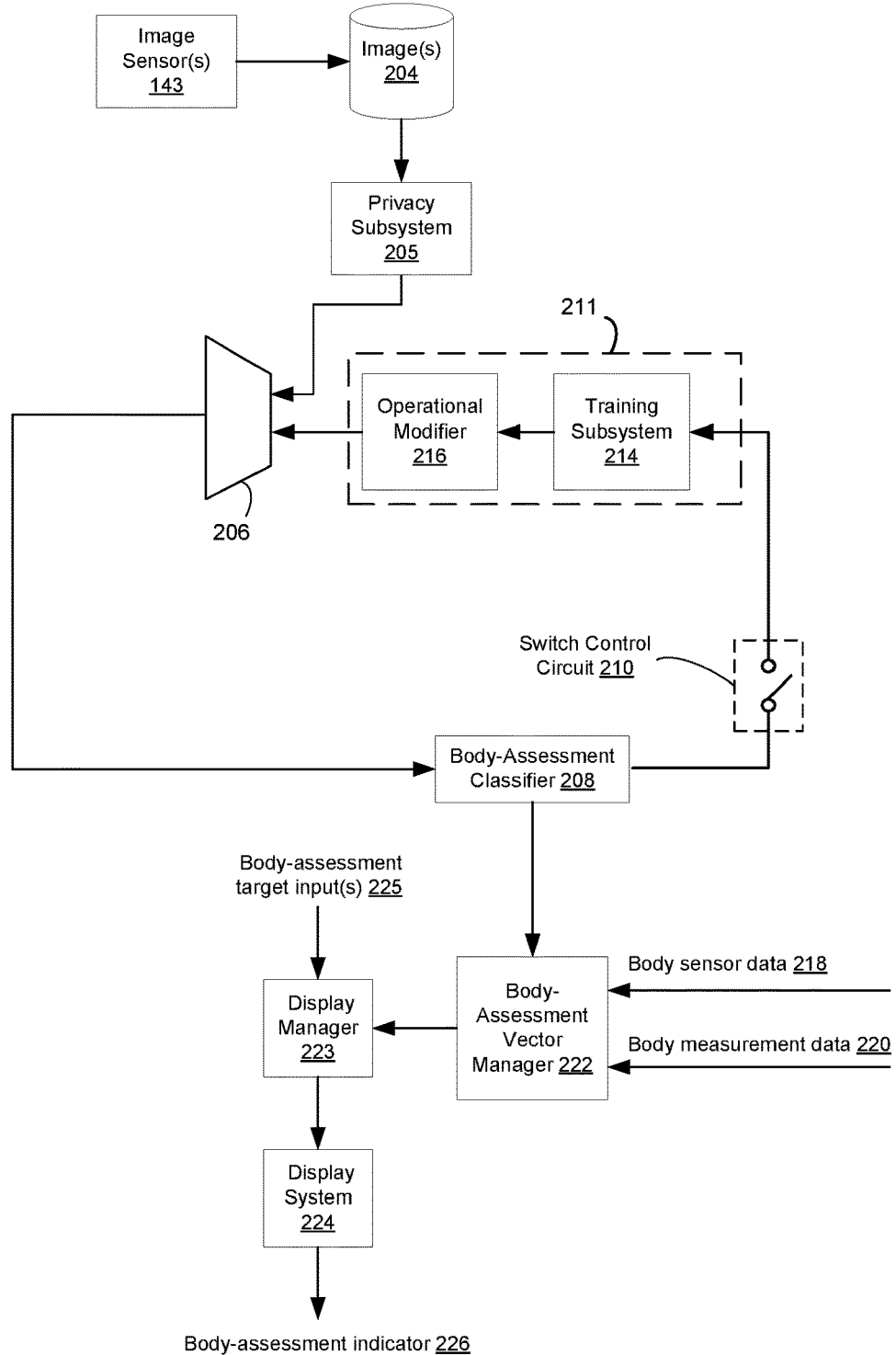
FIG. 2 is a block diagram of a fitness system for training a body-assessment classifier and utilizing the body-assessment classifier in order to generate body-assessment indicators in accordance with some implementations.

FIG. 2 is a block diagram of a fitness system 200 for training a body-assessment classifier 208 and utilizing the body-assessment classifier 208 in order to generate body-assessment indicators 226 in accordance with some implementations. In various implementations, the fitness system 200 includes some or all of the components of the electronic device 100 in FIG. 1. For example, in some implementations, the fitness system 200 includes a peripherals interface 118, CPU(s) 120, and a memory controller 122 for processing and storage resources. As another example, in some implementations, the fitness system 200 allocates, within a memory 102, the image(s) datastore 204.

In various implementations, the fitness system 200 or portions thereof are included in a device or system enabled with one or more machine-listening applications, such as a communication device included in an autonomous vehicle, a computer; a laptop computer; a tablet device; a mobile phone; a smartphone; a wearable device (e.g., a smart watch); a gaming device; a hearing aid; an Internet-of-things (IOT) device; a computer generated reality (CGR) device (e.g., HMD, heads-up display) that displays CGR content, such as augmented reality (AR) content, virtual reality (VR) content, and/or mixed-reality content (MR) content; and/or the like.

While pertinent features are illustrated, those of ordinary skill in the art will appreciate from the present disclosure that various other features have not been illustrated for the sake of brevity and so as not to obscure more pertinent aspects of the implementations disclosed herein. Those of ordinary skill in the art will also appreciate from the present disclosure that the functions and sub-functions implemented by the fitness system 200 can be combined into one or more systems and/or further sub-divided into additional subsystems: and, that the functionality described below is provided as merely one example configuration of the various aspects and functions described herein.

To that end, as a non-limiting example, the fitness system 200 includes one or more image sensors 143, an image(s) datastore 204, a privacy subsystem 205, a mode-selection multiplexer (MUX) 206, a body-assessment classifier 208, a switch control circuit 210, a training system 211, body sensor data 218, body measurement data 220, a body-assessment vector manager 222, a display manager 223, a display system 224, body-assessment target input(s) 225, and a body-assessment indicator 226.

The image sensor(s) 143 (e.g., forward-facing camera, HMD camera) capture still images or moving images (e.g., video stream) including a user. The image sensor(s) 143 are provided to receive and convert the images into image data. In some implementations, the fitness system 200 stores the image data in the image(s) datastore 204 (e.g., a non-transitory memory). In some implementations, the image(s) datastore 204 is populated independently of image data from the image sensor(s) 143. For example, the fitness system 200 obtains image data from the Internet or from another electronic device, such as a smartphone or wearable device (e.g., smartwatch).

In various implementations, the fitness system 200 includes a privacy subsystem 205 that includes one or more privacy setting filters associated with user information, such as user information included in the image(s) datastore 204, the body sensor data 218, the body measurement data 220, and/or other identifying information. In some implementations, the privacy subsystem 205 selectively prevents and/or limits the fitness system 200 or portions thereof from obtaining and/or transmitting the user information. To this end, the privacy subsystem 205 receives user preferences and/or selections from the user in response to prompting the user for the same. In some implementations, the privacy subsystem 205 prevents the fitness system 200 from obtaining and/or transmitting the user information unless and until the privacy subsystem 205 obtains informed consent from the user. In some implementations, the privacy subsystem 205 anonymizes (e.g., scrambles or obscures) certain types of user information. For example, the privacy subsystem 205 receives user inputs designating which types of user information the privacy subsystem 205 anonymizes. As another example, the privacy subsystem 205 anonymizes certain types of user information likely to include sensitive and/or identifying information, independent of user designation (e.g., automatically).

In some implementations, the mode-selection MUX 206 coordinates switching between a training mode and a detection (e.g., run-time) mode with respect to the body-assessment classifier 208. In some implementations, operation of the mode-selection MUX 206 is managed by a system controller (not shown) or operating system (e.g., the operating system 907 in FIG. 9).

In training mode, the mode-selection MUX 206 couples the training system 211 to the body-assessment classifier 208 in order to enable training of the body-assessment classifier 208. In the training mode, the fitness system 200 sets the switch control circuit 210 to "on" (e.g., closes the switch) so that output of the body-assessment classifier 208 is provided to the training system 211. In some implementations, the training system 211 is provided separately. Operation of the training system 211, including a training subsystem 214 and an operational modifier 216, will be detailed further, below, with reference to FIG. 3.

In detection (e.g., run-time) mode, on the other hand, the mode-selection MUX 206 couples the image data stored in the image(s) datastore 204 to the body-assessment classifier 208. In the detection mode, the fitness system 200 sets the switch control circuit 210 to "off" (e.g., opens the switch) so that output of the body-assessment classifier 208 is not provided to the training system 211. According to various implementations, in the detection mode, the trained body-assessment classifier 208 displays the body-assessment indicator 226 that indicates body-assessments values associated with a user. To that end, the body-assessment classifier 208 obtains one or more images associated with the user (e.g., stored image(s) 204). Based on the one or more images, the body-assessment classifier 208 generates one or more body-assessment vectors (e.g., body-assessment vectors 410-1 . . . 410-M in FIG. 4) that include quantitative physique and biometric assessments associated with the user.

In some implementations, the body-assessment classifier 208 provides the one or more body-assessment vectors to a display manager 223. The display manger 223 displays, via a display system 224, a body-assessment indicator 226 that is based on the one or more body-assessment vectors. In some implementations, the body-assessment indicator 226 includes a visual representation of a user (e.g., spatial or volumetric model) that is based on the one or more body-assessment vectors.

In some implementations, the display manager 223 receives one or more body-assessment target inputs 225 specifying one or more body-assessment targets, such as "Lose 10 pounds" or "Enlarge biceps." In some implementations, in accordance with a determination that the one or more body-assessment vectors from the body-assessment classifier 208 satisfy the one or more body-assessment targets, the display manager 223 displays a successful target indication. Moreover, in some implementations, the display manager 223 modifies the visual representation of the user based on the one or more body-assessment targets so that the modified visual representation or portions thereof reflect the body-assessment targets, rather than the current body-assessments of the user.

According to various implementations, the body-assessment vector manager 222 modifies the one or more body-assessment vectors from the body-assessment classifier 208, and the display manager 223 displays a body-assessment indicator 226 that is based on the modified one or more body-assessment vectors. For example, the body-assessment vector manager 222 modifies the one or more body-assessment vectors based on body sensor data 218, such as heartrate data obtained from a wearable device (e.g., a smartwatch). As another example, the body-assessment vector manager 222 modifies the one or more body-assessment vectors based on body measurement data 220, such as based on input(s) obtained from a user, such as the user's heartrate, weight, height, BMI, and/or the like.

Figure 3:
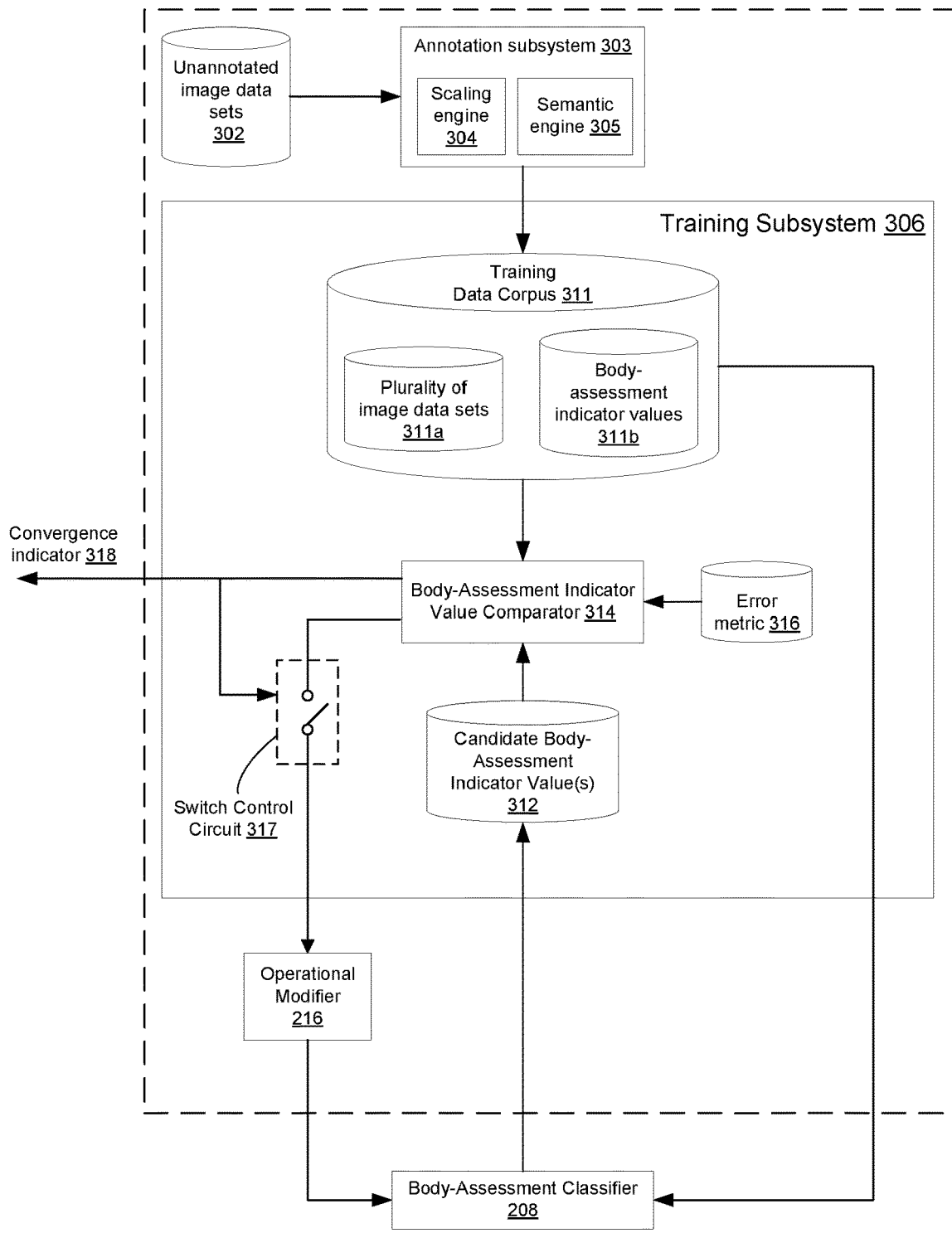
FIG. 3 is a block diagram of an example of a training system for training a body-assessment classifier in accordance with some implementations.

FIG. 3 is a block diagram of an example of a training system 300 for training a body-assessment classifier 208 in accordance with some implementations. While pertinent features are illustrated, those of ordinary skill in the art will appreciate from the present disclosure that various other features have not been illustrated for the sake of brevity and so as not to obscure more pertinent aspects of the implementations disclosed herein. Those of ordinary skill in the art will also appreciate from the present disclosure that the functions and sub-functions implemented by the training system 300 can be combined into one or more systems and/or further sub-divided into additional subsystems: and, that the functionality described below is provided as merely one example configuration of the various aspects and functions described herein. In some implementations, the training system 300 or portions thereof are similar to and adapted from the training system 211 in FIG. 2. To that end, as a non-limiting example, the training system 300 includes a body-assessment classifier 208, an operational modifier 216, a plurality of unannotated image data sets stored in a datastore 302, an annotation subsystem 303, and a training subsystem 306. In some implementations, the training subsystem 306 or portions thereof are similar to and adapted from the training subsystem 214 in FIG. 2.

The training subsystem 306 includes a training data corpus datastore 311 that includes a plurality of image data sets 311a. Each of the plurality of image data sets 311a is associated with a respective individual. For example, a particular image data set includes a top-down clothed image of a particular individual, a shirtless front view image of the particular individual, and a shirtless side view image of the particular individual. Each of the plurality of image data sets 311a is associated with respective one or more body-assessment indicator values 311b, and the respective one or more body-assessment indicator values 311b are visually assessable. As will be described below, the respective one or more body-assessment indicator values 311b provide a baseline (e.g., known value) against which to compare candidate (e.g., estimated) corresponding values generated by the body-assessment classifier 208.

According to various implementations, the training system 300 utilizes the plurality of image data sets 311a and the respective one or more body-assessment indicator values 311b to train the body-assessment classifier 208. Namely, the body-assessment classifier 208 generates at least one candidate body-assessment indicator value corresponding to a portion of the plurality of image data sets 311a. The training subsystem 306 may store the at least one candidate body-assessment indicator value in a corresponding datastore 312.

In some implementations, each of the plurality of image data sets 311a includes annotation data providing quantitative values corresponding to the respective one or more body-assessment indicator values 311b. For example, a particular image of the plurality of image data sets 311a includes annotation labels of "male", "155 pounds", "13% bodyfat percentage", etc.

In various implementations, the training system 300 includes an annotation subsystem 303. The annotation subsystem 303 generates a plurality of annotation values corresponding to a plurality of unannotated image data sets 302. The annotation subsystem 303 provides the plurality of unannotated image data sets 302 and corresponding annotation values to the training data corpus 311. In some implementations, the training system 300 stores the plurality of unannotated image data sets 302 in the plurality of image data sets datastore 311a and stores the corresponding annotation values in the body-assessment indicator values datastore 311b.

In various implementations, the annotation subsystem 303 includes a scaling engine 304 and a semantic engine 305. The scaling engine 304 and the semantic engine 305 facilitate generation of the corresponding annotation values. In some implementations, the scaling engine 304 and the semantic engine 305 cooperate in order to facilitate generation of the corresponding annotation values. In some implementations, the annotation subsystem 303 utilizes one of the scaling engine 304 and the semantic engine 305 in generating the corresponding annotation values.

According to various implementations, the scaling engine 304 determines measurement values of one or more reference objects within a particular one of the plurality of unannotated image data sets 302. The scaling engine 304 determines a scaling factor based on the measurement values and generates a particular annotation value corresponding to the particular one of the plurality of unannotated image data sets 302 based on the scaling factor. Further details about the scaling engine 304 are provided below, with respect to FIG. 7.

According to various implementations, the semantic engine 305 generates a plurality of semantic values that correspond to the plurality of unannotated image data sets 302. Each of the plurality of semantic values semantically characterizes a corresponding one of the plurality of unannotated image data sets 302. Each of the plurality of annotation values is a function of a respective one of the plurality of semantic values. Further details about the semantic engine 305 are provided below; with respect to FIG. 7.

A body-assessment indicator value comparator 314 compares the at least one candidate body-assessment indicator value 312 against a corresponding body-assessment indicator value 311b within the training data corpus 311. In response to determining that a result of the comparison does not satisfy an error metric 316, the body-assessment indicator value comparator 314 directs the operational modifier 216 to modify an operational value of the body-assessment classifier 208. In some implementations, the body-assessment indicator value comparator 314 outputs a convergence indicator 318 having a value of zero, in turn turning on (e.g., closing) a switch-control circuit 317 in order to enable the body-assessment indicator value comparator 314 to direct the operational modifier 216. In some implementations, the error metric 316 is not satisfied when the training subsystem 306 has not finished sufficiently training the body-assessment classifier 208.

On the other hand, in response to determining that the result of the comparison satisfies the error metric 316 and that the training data corpus 311 is sufficiently utilized, the body-assessment indicator value comparator 314 outputs a convergence indicator 318 having a value of one. Accordingly, the training subsystem 306 turns off (e.g., opens) the switch-control circuit 317, which in turn disables the body-assessment indicator value comparator 314 from directing the operational modifier 216 to modify an operational value of the body-assessment classifier 208. In some implementations, the error metric 316 is satisfied when the training subsystem 306 has sufficiently trained the body-assessment classifier 208. In some implementations, the body-assessment classifier 208 is sufficiently trained when the body-assessment classifier 208 has processed (e.g., classified) a threshold percentage of the plurality of image data sets 311a. In some implementations, the body-assessment classifier 208 is sufficiently trained when the body-assessment classifier 208 has processed a threshold number (e.g., a raw number) of the plurality of image data sets 311a.

FIG. 4 is an example of a representation 400 of body-assessment vectors according to some implementations. Each of the body-assessment vectors 410-1 . . . 410-M is a function of a particular one of one or more images associated with a user. The body-assessment vectors 410-1 . . . 410-M include quantitative physique and biometric assessments associated with the user. As will be described further with respect to FIGS. 6A-6L, in run-time mode an electronic device 100 displays a body-assessment indicator that is based on the one or more body-assessment vectors 410-1 . . . 410-M. One of ordinary skill in the art will appreciate that various types of values may be included within each body-assessment vector, and that the examples provided below are merely illustrative and not exhaustive.

As one example, as illustrated in FIG. 4, a first body-assessment vector 410-1 is associated with a first image 420-1 that is a side view of a user, John Doe. The first body-assessment vector includes the following quantitative physique and biometric assessment associated with John Doe: a gender value 430a-1, a bodyfat value 430b-1, a weight value 430c-1, and optionally other various sub-values. For example, although not illustrated, the gender value 430-1 is "0" to indicate that John is a male (e.g., "0")

has been set to represent males and "1" to represent females), the bodyfat value 430b-1 is "18" to indicate that John has 18 percent bodyfat, and the weight value 430c-1 is "135" to indicate that John weighs 135 pounds. Moreover, a second body-assessment vector 410-2 is associated with a second image 420-2 of John Doe, such as top-down image of John. However, the second body-assessment vector 410-2 includes a weight value 430c-2 of "140" corresponding to 140 pounds. Thus, according to various implementations, the fitness system utilizes both the value "135" for the weight value 430c-1 and the value "140" for the weight value 430c-2 in order to determine a more accurate weight estimate for John. For example, the fitness system may average the two values to determine that John weighs 137.5 pounds.

As another run-time example, as illustrated in FIG. 4, a third body-assessment vector 410-3 is associated with a rear image 420-3 of a different user, Jane Doe. The third body-assessment vector 410-3 includes a gender value 430a-3 of "1" to indicate that Jane is a female. Moreover, although not illustrated, the third body-assessment vector 410-3 includes the following body-assessment sub-values associated with Jane: height of 63 inches, waist size of 30 inches, BMI of 11, and a body type value of "2" (e.g., severely underweight is "0," underweight is "1," fit is "2," muscular is "3," overweight is "4," and severely overweight is "5"). One of ordinary skill in the art will appreciate that the fitness system may include various body-assessment sub-values that are quantitatively defined in various ways.

Figure 5:
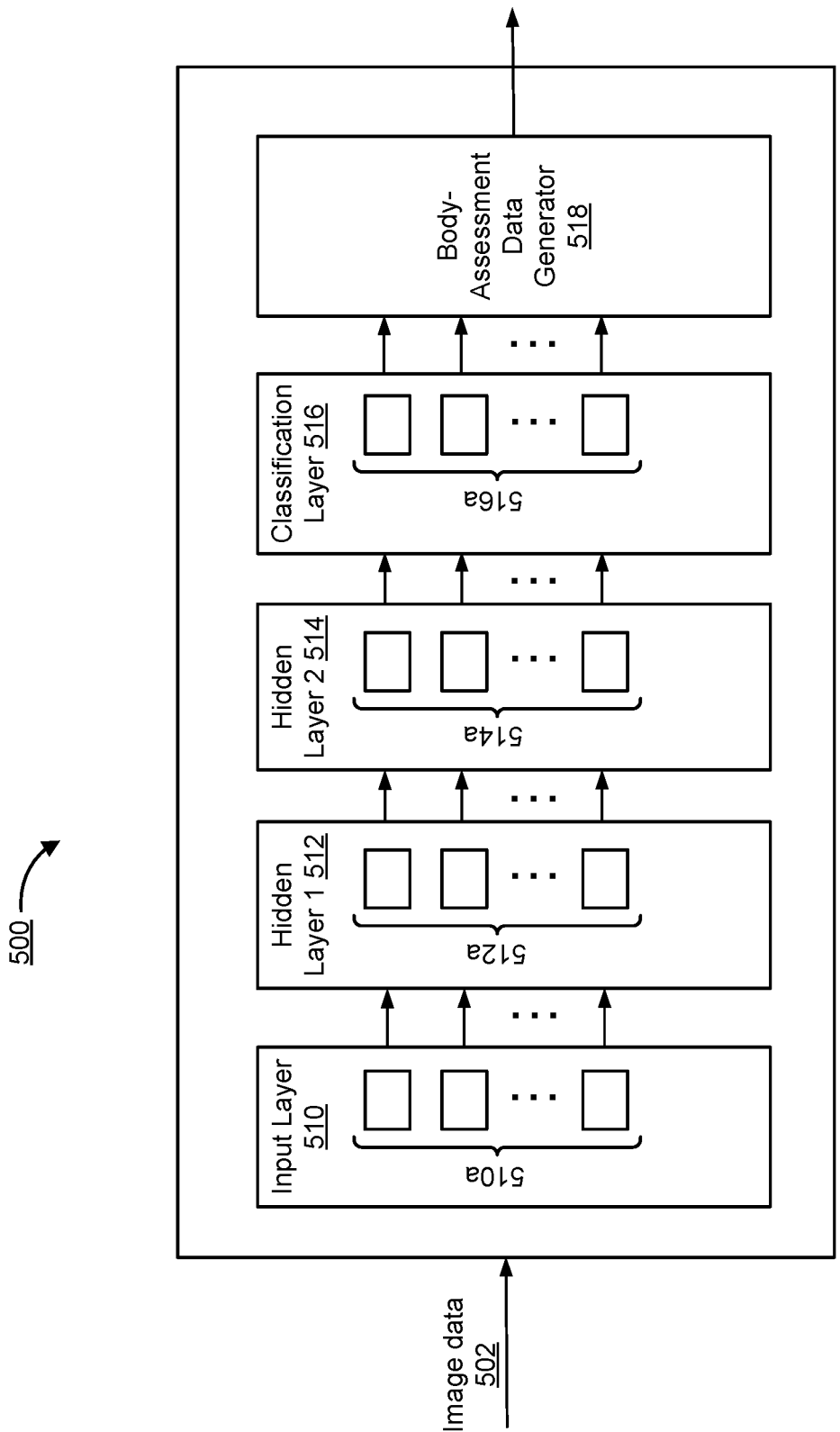
FIG. 5 is a block diagram of an example of a neural network according to some implementations.

FIG. 5 is a block diagram of an example of a neural network according 500 to some implementations. According to various implementations, the neural network 500 corresponds to or integrated within the body-assessment classifier 208 in FIG. 2 and/or FIG. 3. For example, in training mode a body-assessment data generator 518 included in the neural network 500 generates at least one candidate body-assessment indicator value (e.g., candidate body-assessment indicator value(s) 312 in FIG. 3) based on image data 502. The image data 502 may correspond to a portion of a plurality of image data sets. As illustrated in FIG. 3, the training subsystem 306 trains, via an operational modifier 216, the body-assessment classifier 208 based on a comparison between the at least one candidate body-assessment indicator value and a corresponding body-assessment indicator value. The corresponding body-assessment indicator value may correspond to a body-assessment indicator value 311b in FIG. 3. As another example, in run-time (e.g., detection) mode the body-assessment data generator 518 generates one or more body-assessment vectors associated with a user. The one or more body-assessment vectors are based on image data 502 associated with the user, such as image data stored in the image(s) datastore 204 in FIG. 2. As illustrated in FIG. 2, based on the one or more body-assessment vectors, the fitness system 200 displays a body-assessment indicator 226 via a display system 224 according to various implementations.

In the example of FIG. 5, the neural network 500 includes an input layer 510, a first hidden layer 512, a second hidden layer 514, a classification layer 516, and a body-assessment data generator 518. While the neural network 500 includes two hidden layers as an example, those of ordinary skill in the art will appreciate from the present disclosure that one or more additional hidden layers are also present in various implementations. Adding additional hidden layers adds to the computational complexity and memory demands, but may improve performance for some applications.

In various implementations, the input layer 510 is coupled (e.g., configured) to receive various inputs. For example, in some implementations, the input layer 510 receives image data 502, such as from the image(s) datastore 204 in FIG. 2 and/or the plurality of image data sets 311a in FIG. 3. In various implementations, the input layer 510 includes a number of LSTM logic units 510a, which are also referred to as model(s) of neurons by those of ordinary skill in the art. In some such implementations, an input matrix from the features to the LSTM logic units 510a include rectangular matrices. The size of this matrix is a function of the number of types of input data (e.g., number of images, type of images (e.g., still versus moving), size of images, resolution of images, etc.) included in the image data 502.

In some implementations, the first hidden layer 512 includes a number of LSTM logic units 512a. In some implementations, the number of LSTM logic units 512a ranges between approximately 10-500. Those of ordinary skill in the art will appreciate that, in such implementations, the number of LSTM logic units per layer is orders of magnitude smaller than previously known approaches (being of the order of $O(10^1)$-$O(10^2)$), which enables such implementations to be embedded in highly resource-constrained devices. As illustrated in the example of FIG. 5, the first hidden layer 512 receives its inputs from the input layer 510.

In some implementations, the second hidden layer 514 includes a number of LSTM logic units 514a. In some implementations, the number of LSTM logic units 514a is the same as or similar to the number of LSTM logic units 510a in the input layer 510 or the number of LSTM logic units 512a in the first hidden layer 512. As illustrated in the example of FIG. 5, the second hidden layer 514 receives its inputs from the first hidden layer 512. Additionally or alternatively, in some implementations, the second hidden layer 514 receives some or all of its inputs from the input layer 510.

In some implementations, the classification layer 516 includes a number of LSTM logic units 516a. In some implementations, the number of LSTM logic units 516a is the same as or similar to the number of LSTM logic units 510a in the input layer 510, the number of LSTM logic units 512a in the first hidden layer 512, or the number of LSTM logic units 514a in the second hidden layer 514. In some implementations, the classification layer 516 performs a multinomial logistic function (e.g., a soft-max function) that produces a number of outputs.

In some implementations, the body-assessment data generator 518 generates various values by selecting the top N action candidates provided by the classification layer 516. In some implementations, the top N action candidates are most likely to accurately characterize corresponding a word combination. In some implementations, the body-assessment data generator 518 generates a set of probability or confidence values for characterizations of corresponding word combinations.

FIGS. 6A-6L are examples of a user interface 600 for a fitness system (e.g., the fitness system 200 in FIG. 2) in accordance with some implementations. As illustrated in FIGS. 6A-6L, the user interface 600 and associated processes are implemented on the portable multifunction device 100 shown in FIG. 1. However, one of ordinary skill in the art will appreciate that the user interface 600 may be implemented on another device, such as a device including greater of fewer of the components of the portable multifunction device 100 in FIG. 1.

Figure 6A:
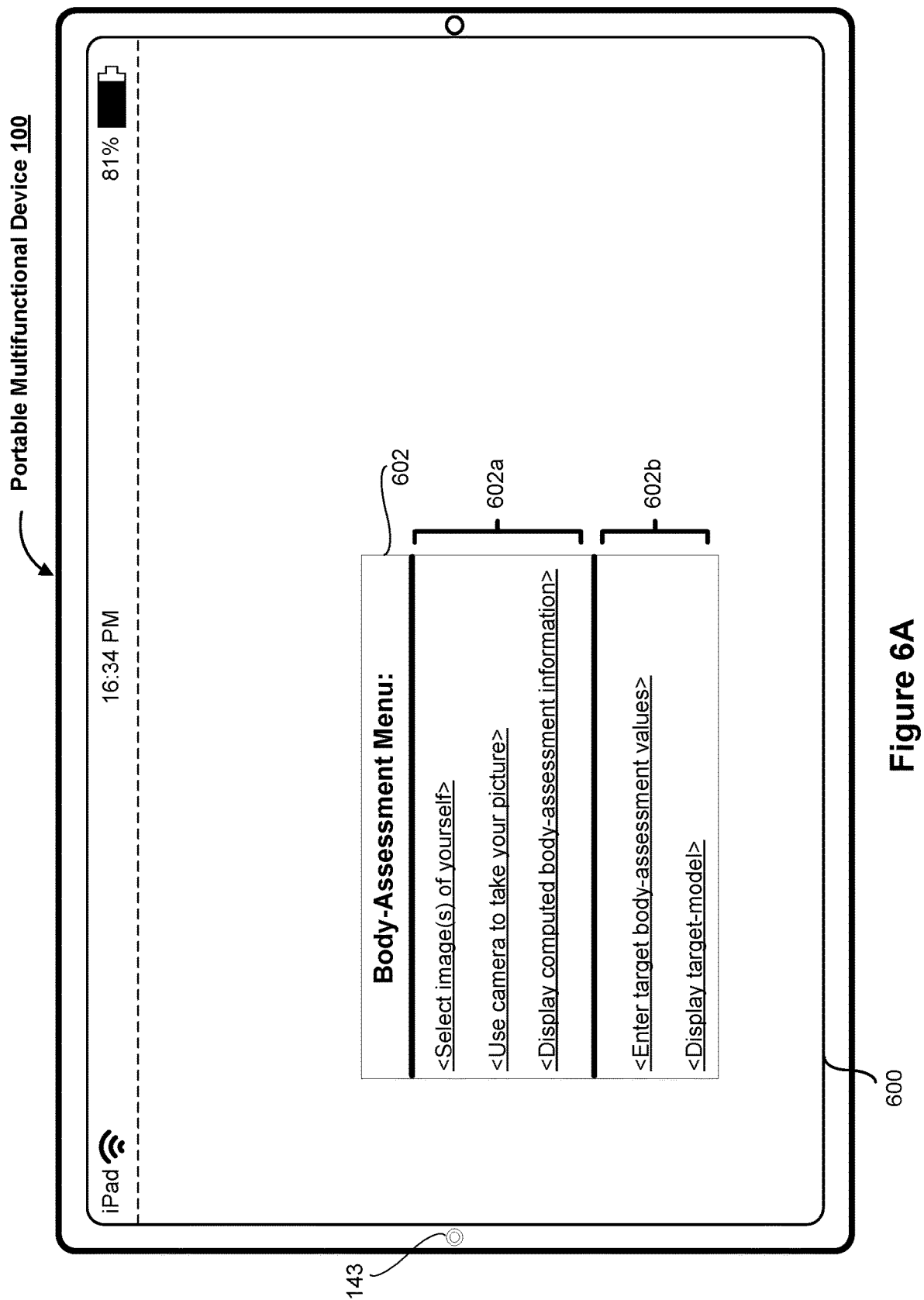

As illustrated in FIG. 6A, the electronic device 100 displays the user interface 600 including a body-assessment menu 602. The body-assessment menu 602 includes a top portion 602a including affordances for obtaining image data associated with a user and displaying corresponding body-assessment information (e.g., a body-assessment indicator) associated with the user. Moreover, as will be detailed, below the body-assessment menu 602 includes a bottom portion 602b including affordances for providing target body visual representations associated with the user.

The top portion 602a of the body-assessment menu 602 includes a "Select image(s) of yourself" affordance for the electronic device 100 to obtain stored (e.g., already generated) image data to be obtained by the electronic device. The top portion 602a of the body-assessment menu 602 also includes a "Use camera to take your picture" affordance for the electronic device 100 to instruct the image sensor 143 to capture a scene including a user and obtain corresponding image data from the image sensor 143.

Figure 6B:
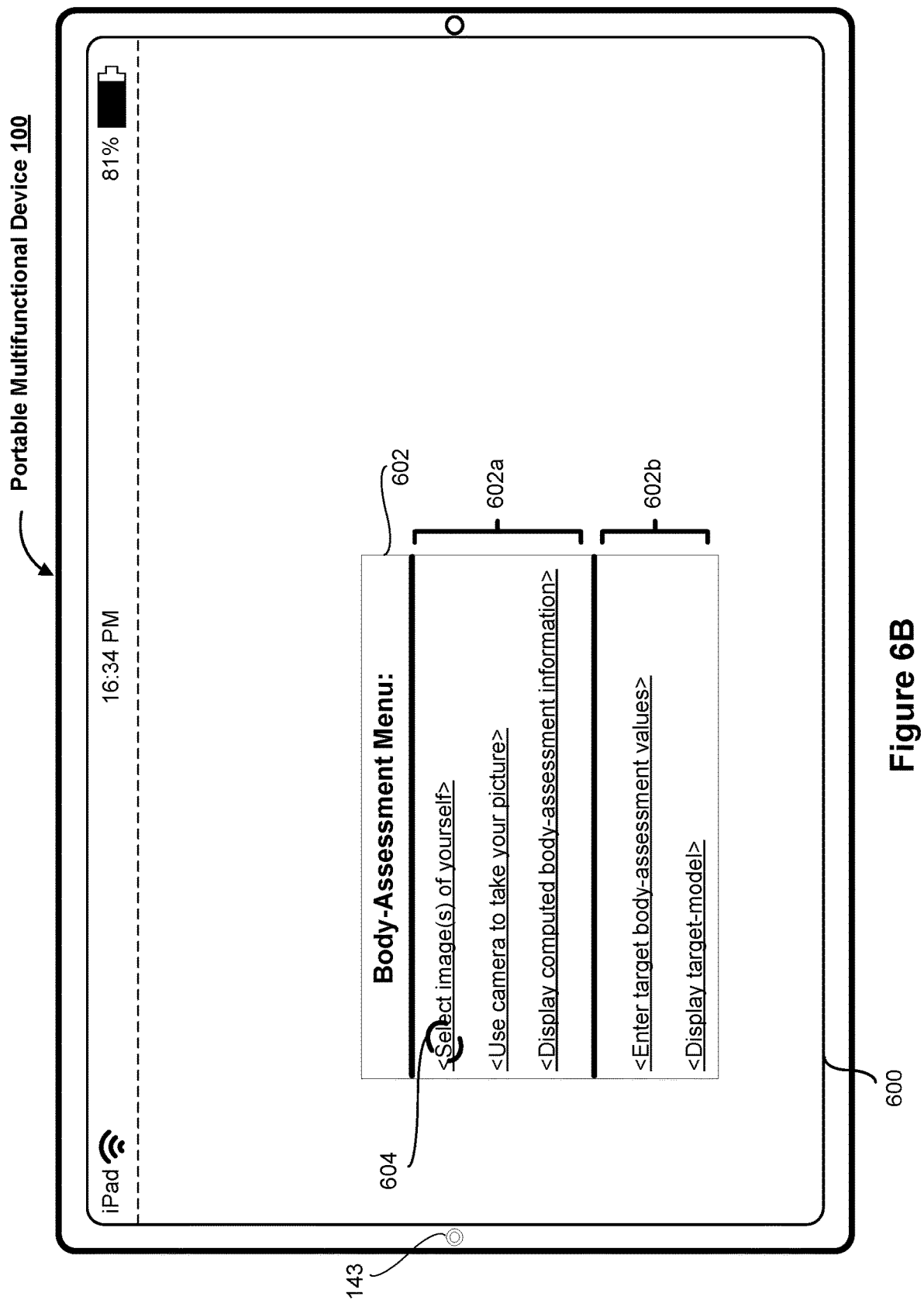

As illustrated in FIG. 6B, the electronic device 100 obtains an input 604 corresponding to the "Select image(s) of yourself" affordance. For example, the input 604 may correspond to an input directed to a touch-sensitive surface of the electronic device 100.

Figure 6C:
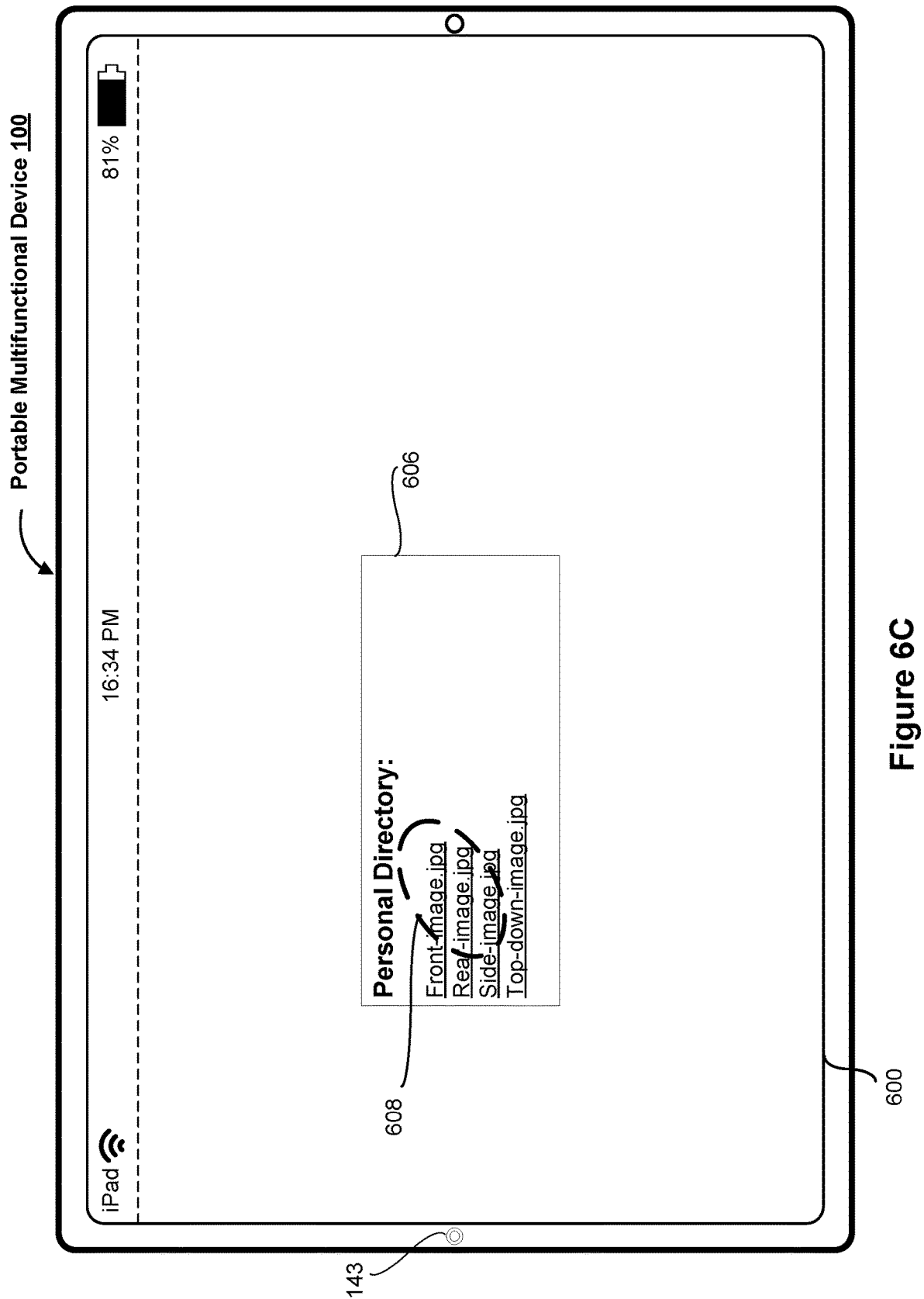

In response to obtaining the input 604 in FIG. 6B, the electronic device 100 displays in FIG. 6C an interface 606 that enables the electronic device 100 to obtain stored image data. The stored image data may reside at any location, such as in local non-transitory memory (e.g., the memory 102 in FIG. 1) and/or remotely (e.g., on the cloud). As illustrated in FIG. 6C, the electronic device 100 obtains an input 608 requesting the electronic device 100 to obtain three stored images associated with a user: "Front-image.jpg," "Rear-image.jpg," and "Side-image.jpg." One of ordinary skill in the art will appreciate that the electronic device 100 may obtain any number of images associated with various filetypes (e.g., .tiff, .bmp, etc.) and/or obtain video data (e.g., .mov, .mpeg, etc.) including a series of images associated with a user.

The electronic device 100 generates, using a body-assessment classifier (e.g., the body-assessment classifier 208 in FIG. 2), three body-assessment vectors. Each of the three body-assessment vectors is a function of a particular one of the three obtained images described above with reference to FIG. 6C. Moreover, the three body-assessment vectors include quantitative physique and biometric assessments associated with the user, such as the various sub-values included in the body-assessment vectors 410-1 . . . 410-M in FIG. 4.

Figure 6D:
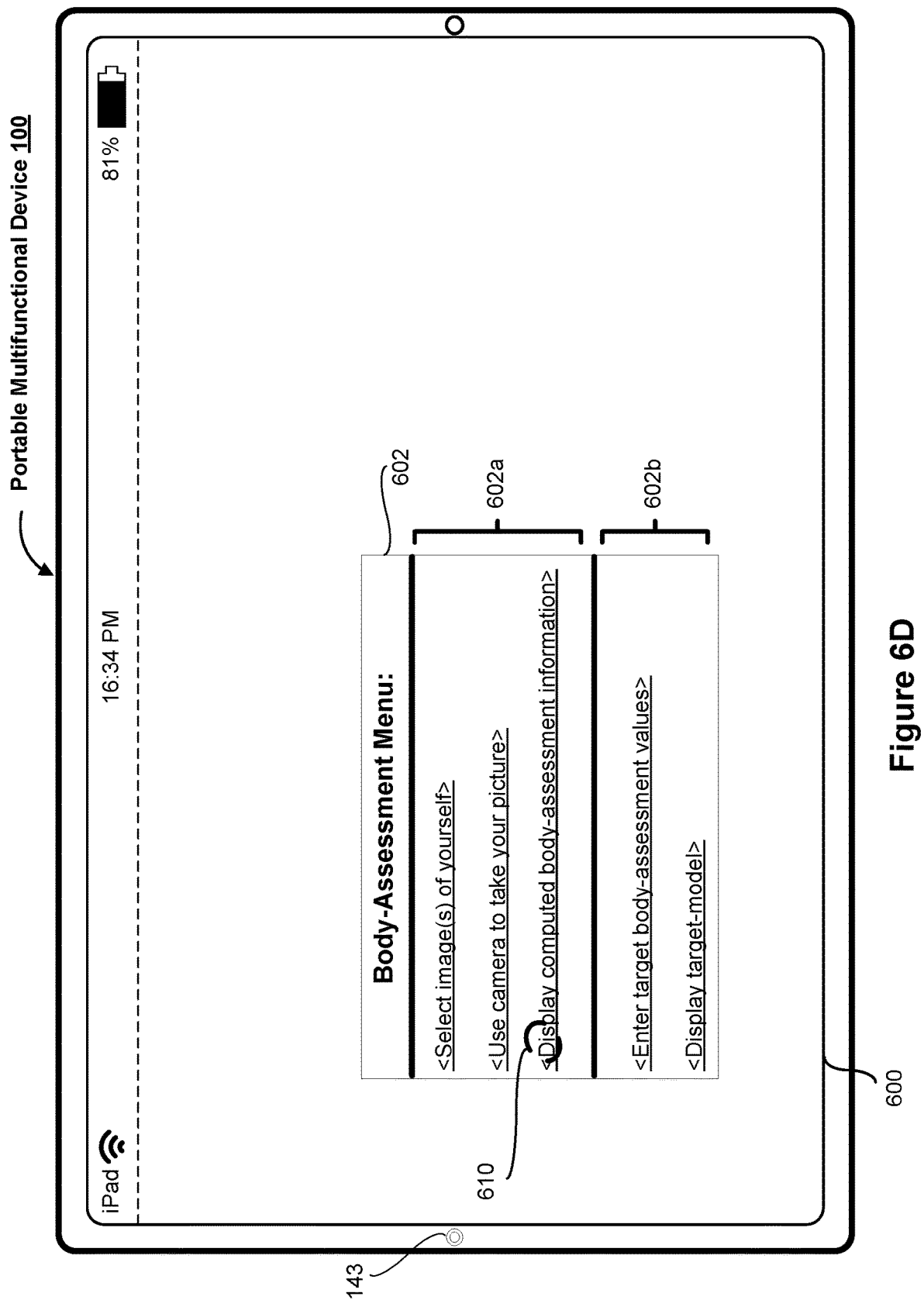

In response to obtaining the input 608 in FIG. 6C, the electronic device 100 redisplays the body-assessment menu 602 in FIG. 6D. As further illustrated in FIG. 6D, the electronic device 100 obtains an input 610 corresponding to a "Display computed body-assessment information" affordance.

Figure 6E:
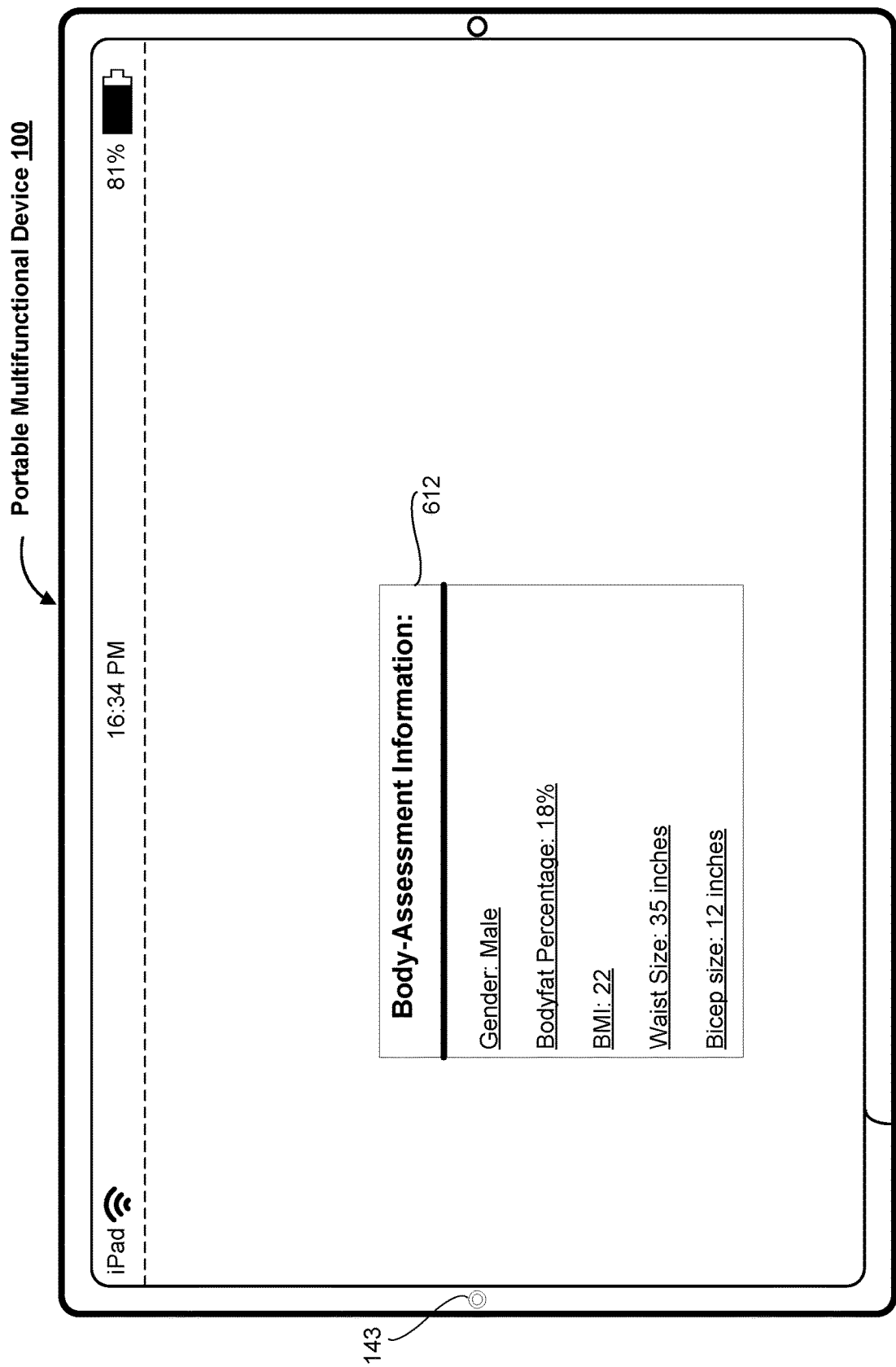

In response to obtaining the input 610 in FIG. 6D, the electronic device 100 displays a body-assessment information interface 612 in FIG. 6E. The body-assessment information interface 612 corresponds to a body-assessment indicator that is based on the three generated body-assessment vectors. As illustrated in FIG. 6E, the body-assessment indicator includes a variety of body-assessment information associated with the user, including the user's gender, bodyfat percentage, BMI, waist size, and bicep size. One of ordinary skill in the art will appreciate that the body-assessment indicator may provide different body-assessment information and/or correspond to a different representation (e.g., a model of the user) of the body-assessment vectors.

Figure 6F:
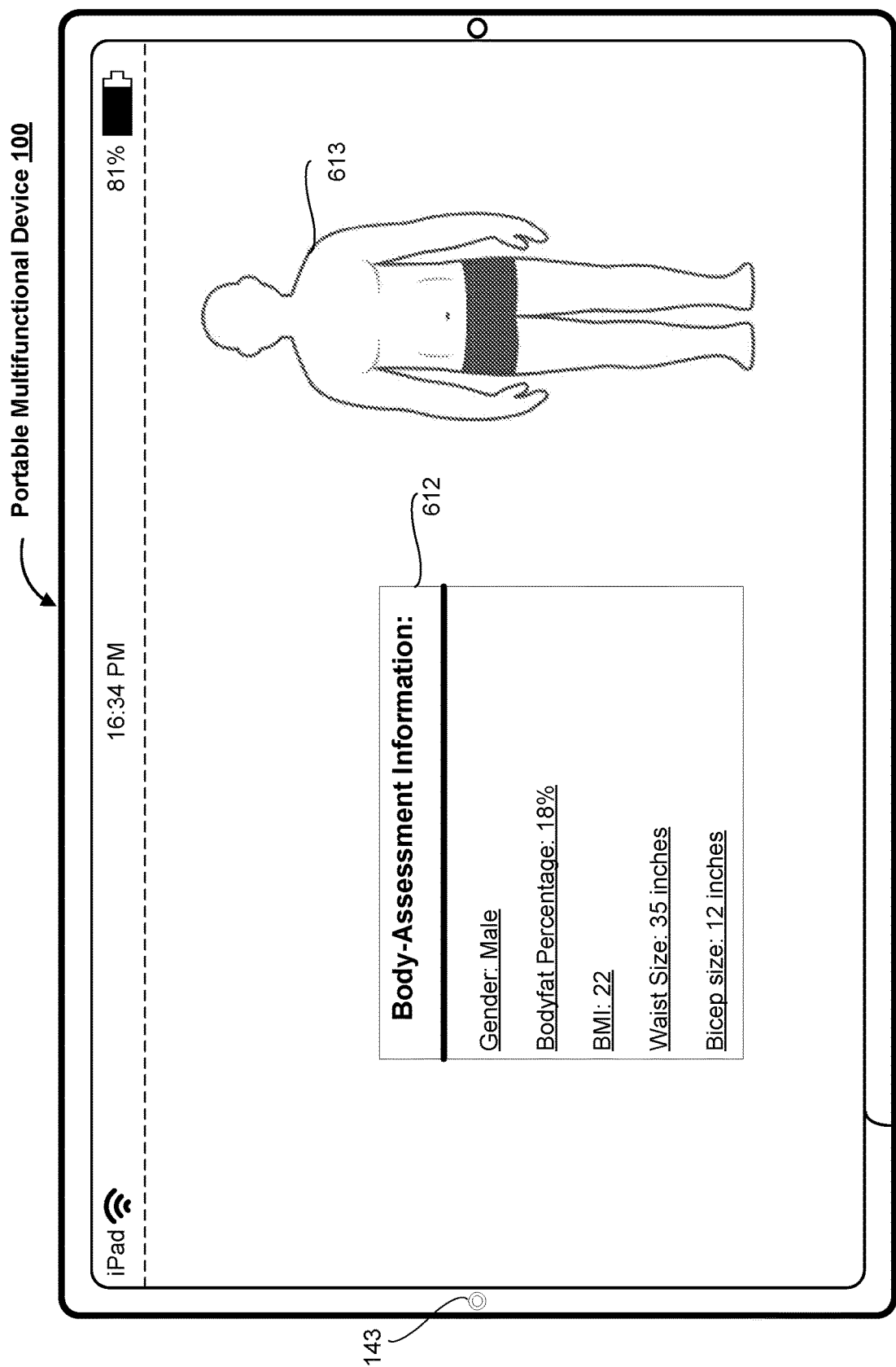

For example, as illustrated in FIG. 6F, in some implementations, in response to obtaining the input 610 in FIG. 6D, the electronic device 100 displays a visual representation (e.g., a model) 613 of the user in addition to the pure textual content included within the body-assessment information interface 612. The electronic device 100 generates the visual representation 613 based on the three body-assessment vectors corresponding to the three images specified via input 608 in FIG. 6C. In other words, the visual representation 613 corresponds to a person who is a male with 18% bodyfat, a BMI of 22, a waist size of 35 inches, and a bicep size of 12 inches.

Figure 6G:
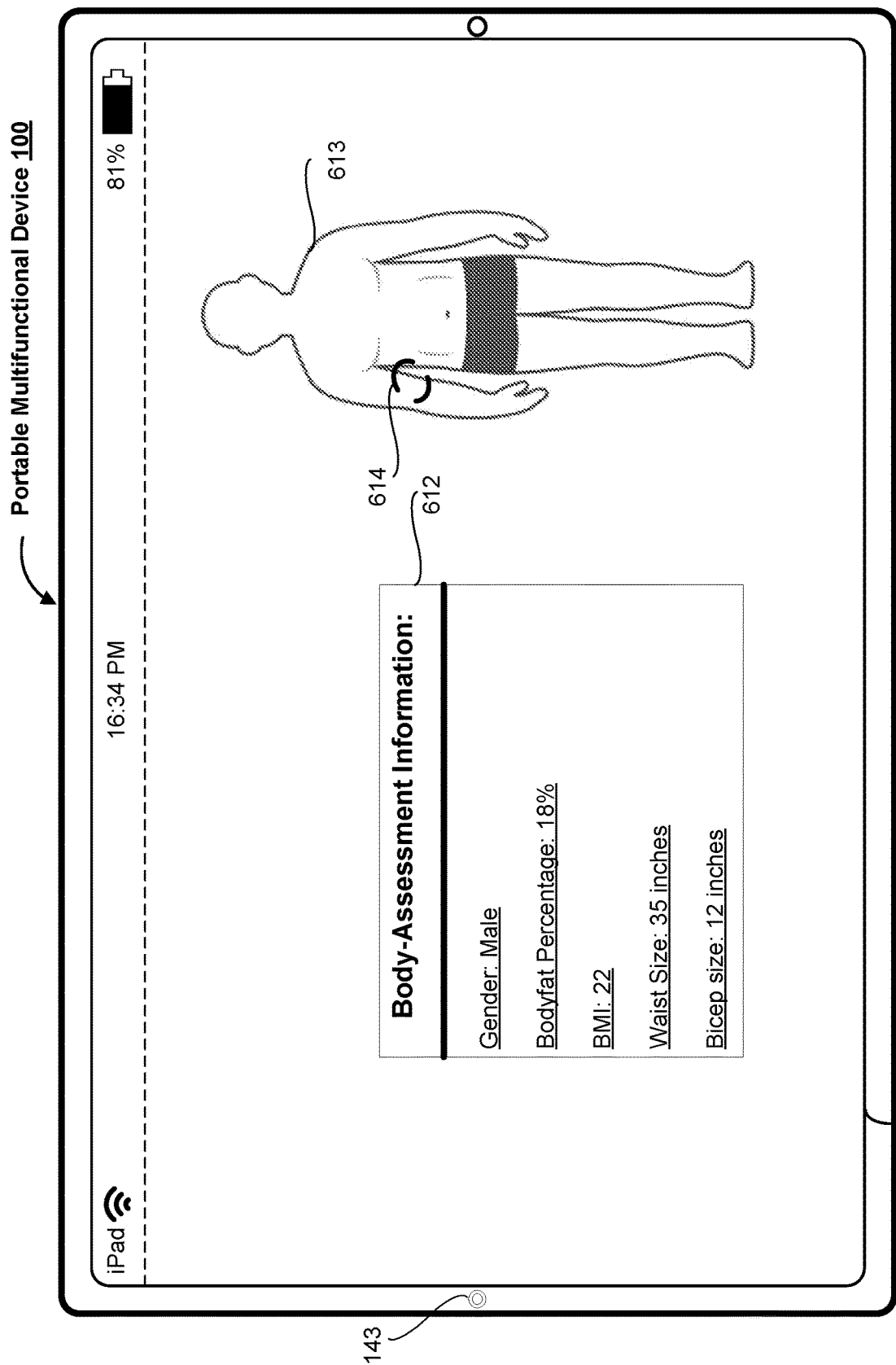

In some implementations, one or more portions of the visual representation 613 correspond to selectable affordances. For example, as illustrated in FIG. 6G, the electronic device 100 obtains an input 614 corresponding to a portion of the visual representation 613. Namely, the input 614 corresponds to a bicep portion of the visual representation 613. In response to obtaining the input 614 in FIG. 6G, the electronic device 100 highlights in FIG. 6H the biceps of the visual representation 613 via interface elements 615a and 615b. One of ordinary skill in the art will appreciate that the electronic device 100 may distinguish an appearance of the biceps of the visual representation 613 from the remainder of the visual representation 613 in a variety of ways, such as by displaying the biceps in a different color or pattern. Moreover, the electronic device 100 displays a body portion indicator 616 indicating bicep information. The body portion indicator 616 indicates that the current bicep size of the user is 12 inches. One of ordinary skill in the art will appreciate that, in response to obtaining an input corresponding to a particular affordance within a visual representation of a user, the electronic device 100 may perform a variety of actions, such as displaying an animation and/or playing an audio clip.

As illustrated in FIGS. 6I-6L, electronic device 100 provides a target (e.g., goal) visual representation of a user according to various inputs corresponding to affordances within the bottom portion of the body-assessment menu 602. According to various implementations, as described above, a trained body-assessment classifier (e.g., the body-assessment classifier 208 in FIG. 2) generates body-assessment vectors based on corresponding image data (e.g., stored images in image datastore 204 in FIG. 2) associated with a user. Based on the body-assessment vectors and body-assessment target input(s) (e.g., the body-assessment target input(s) 225 in FIG. 2), the electronic device 100 generates and displays a target visual representation of a user.

Figure 6H:
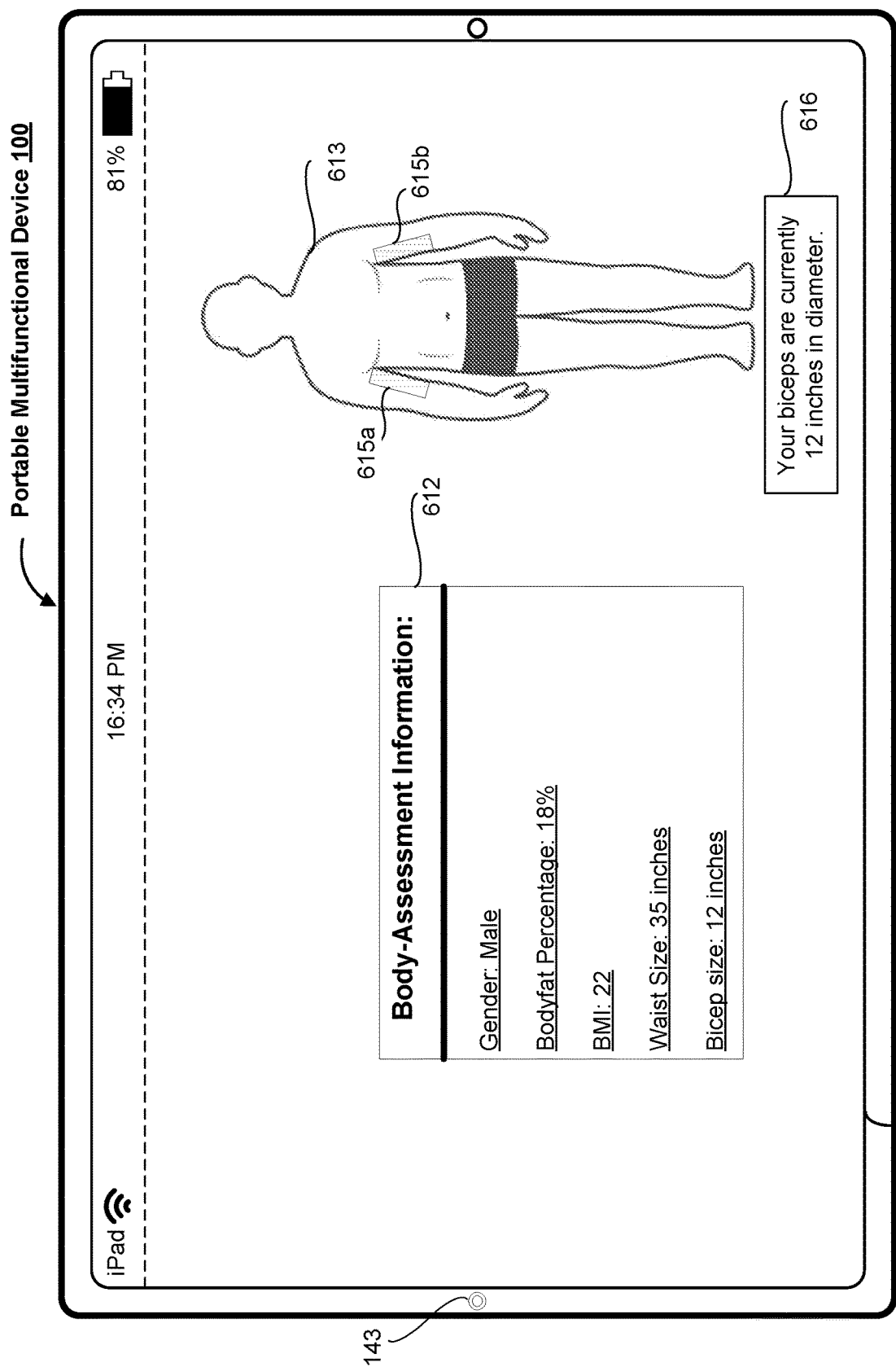
Figure 6I:
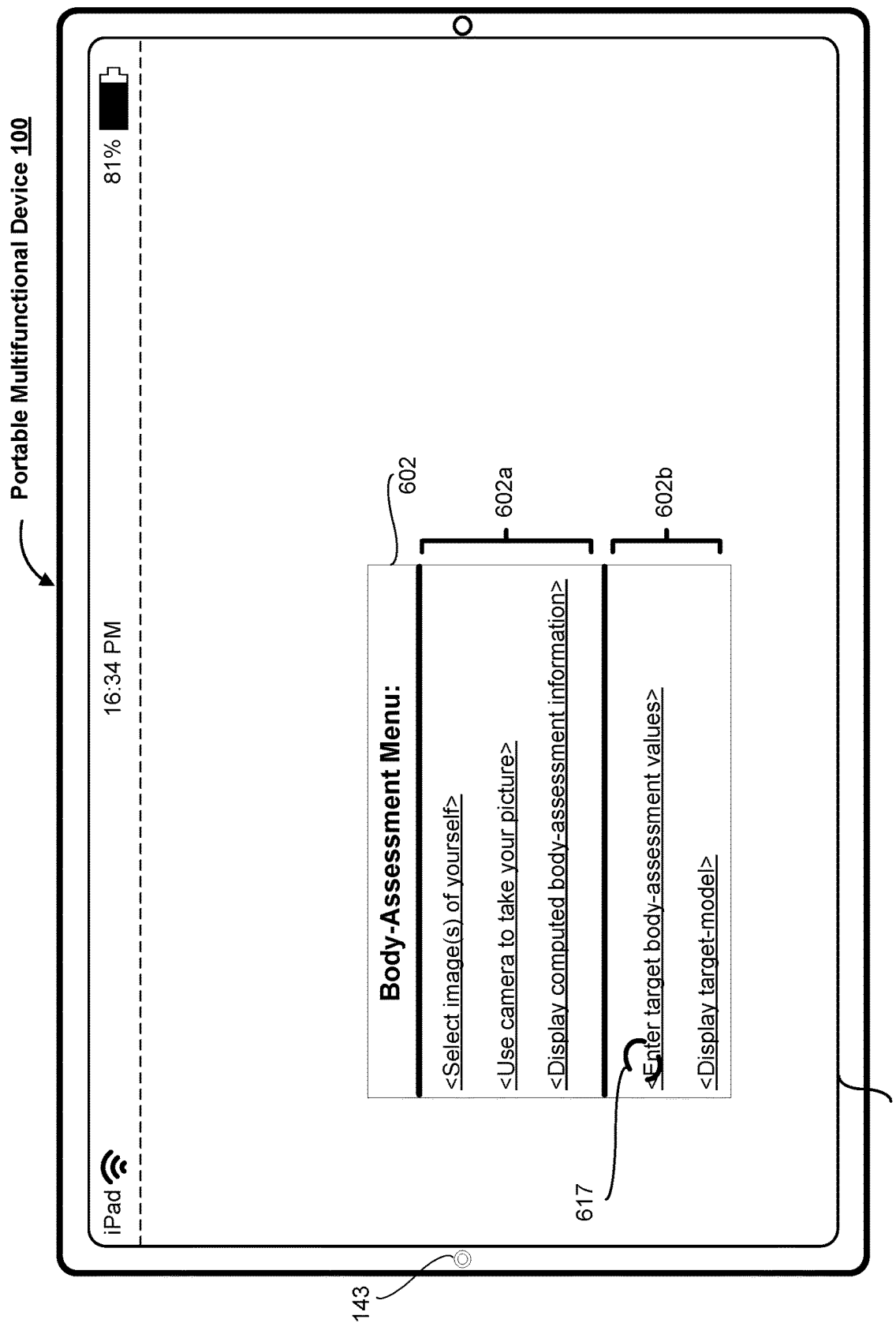

For example, in FIG. 6I the electronic device 100 obtains an input 617 corresponding to an "Enter target body-assessment values" affordance within the bottom portion 602b of the body-assessment menu 602. In response to obtaining the input 617 in FIG. 6I, the electronic device 100 displays an interface 618 in FIG. 6J through which to obtain various body-assessment target input(s). One of ordinary skill in the art will appreciate that, according to various implementations, the interface 618 may include any number and types of body-assessment categories, such as gender, height, body type, BMI, and/or the like. As illustrated in FIG. 6J, the electronic device 100 obtains a waist size target input 620 specifying "less than 32 inches," a bodyfat percentage target input 622 specifying "less than 14%," and a bicep size target input 624 specifying "11 inches or more."

Based on the target inputs 620-624 and the generated body-assessment vectors described with reference to FIGS.

6A-6H, the electronic device 100 generates a target visual representation. The three generated body-assessment vectors corresponding to the three images specified via input 608 in FIG. 6C indicate that the user is a male with 18% bodyfat, a BMI of 22, a waist size of 35 inches, and a bicep size of 12 inches. Moreover, the target inputs 620-624 specify a target waist size of "less than 32 inches," a bodyfat percentage target of "less than 14%," and a bicep size target of "11 inches or more." In some implementations, the electronic device 100 generates the target visual representation by utilizing values included in the three generated body-assessment vectors and replacing certain of these values with corresponding target body-assessment values. Thus, the electronic device 100 generates the target visual representation having the following characteristics; male user as indicted by the body-assessment vectors; 22 BMI as indicted by the body-assessment vectors; waist size of 32 inches specified by corresponding target input 620; bodyfat of 14% specified by corresponding target input 622; and a bicep size of 11 inches specified by corresponding target input 624.

Figure 6K:
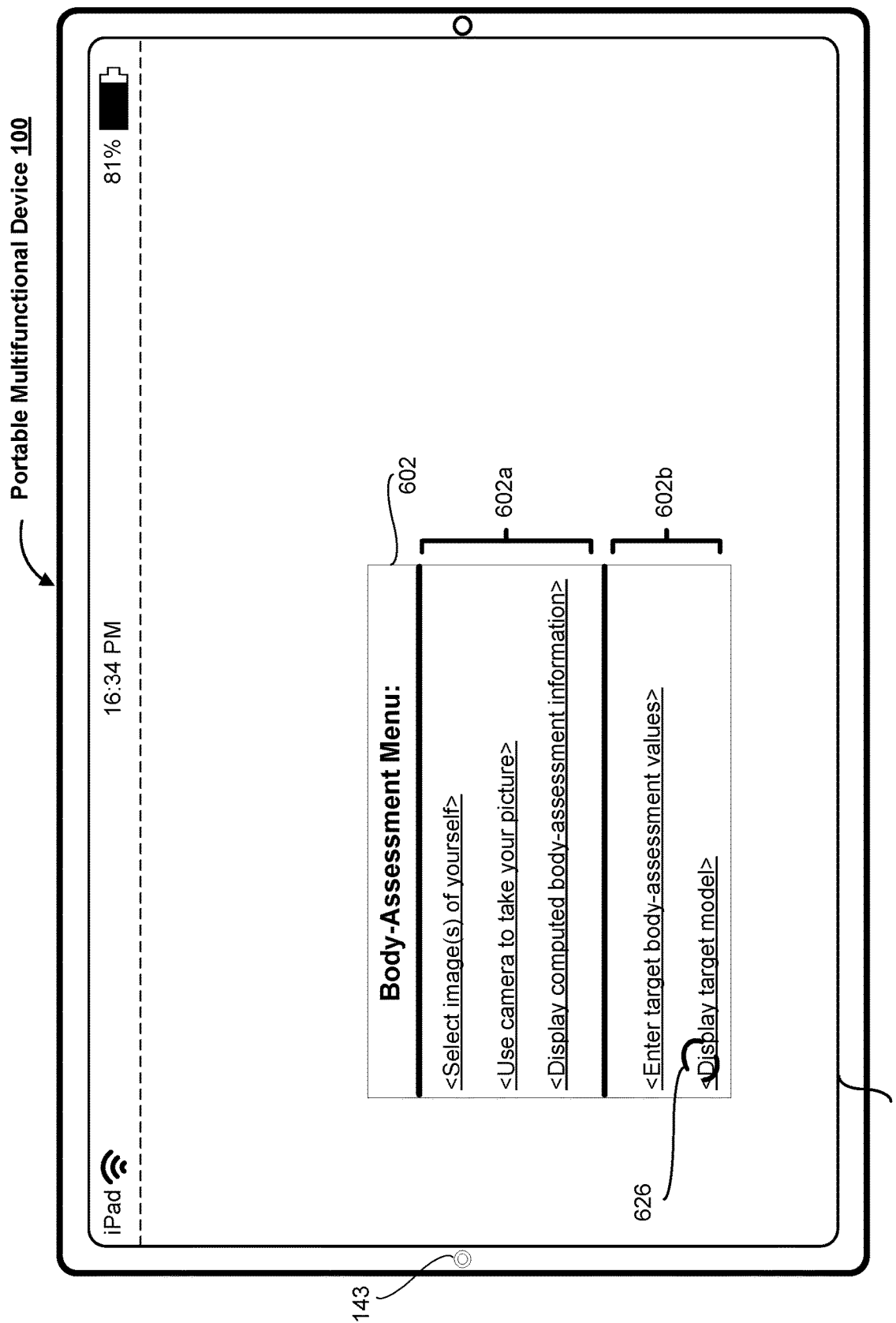

After obtaining the target inputs 620-624 in FIG. 6J, the electronic device 100 displays the body-assessment menu 602 in FIG. 6K. The electronic device 100 obtains an input 626 corresponding to a "Display target model" affordance within the bottom portion 602b of the body-assessment menu 602. In response to obtaining the input 626 in FIG. 6K, the electronic device 100 displays a target visual representation 630 in FIG. 6L. As compared with the visual representation 613 in FIGS. 6F-6H, the target visual representation 630 reflects the target inputs 620-624. Namely, the target visual representation 630 represents a smaller waist size (32 inches versus 35 inches) and a lower body fat percentage (14% versus 18%).

Figure 6L:
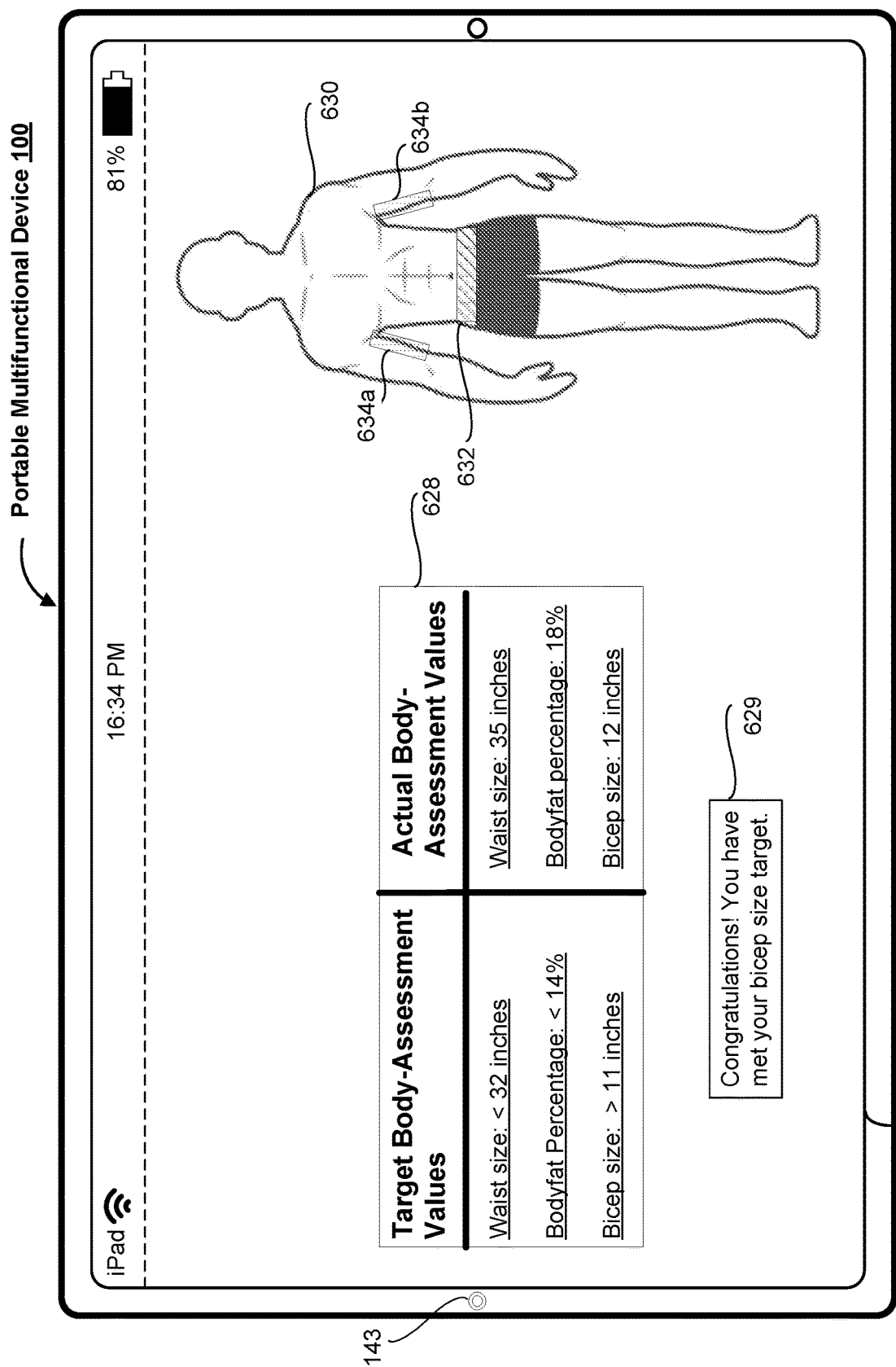

In some implementations, a particular portion of the target visual representation 630 of the user is distinguished from the remainder of the target visual representation 630 of the user. The particular portion of the target visual representation of the user is associated with a particular quantitative physique and biometric assessment that satisfies the one or more body-assessment targets. For example, as illustrated in FIG. 6L, the electronic device 100 distinguishes bicep portions 634a and 634b of the target visual representation 630 because the user's actual bicep size of 12 inches (as indicated in corresponding body-assessment vectors) satisfies the target bicep size specified as greater than 11 inches via input 624 in FIG. 6J. In some implementations, a portion of the target visual representation 630 that does not satisfy the one or more body-assessment targets is distinguished from the remainder of the target visual representation 630 and from the distinguished portion of the target visual representation 630 that satisfies the one or more body-assessment targets. For example, as illustrated in FIG. 6L, the electronic device 100 distinguishes a waist size portion 632 of the target visual representation 630 from the remainder of the target visual representation 630 and from the distinguished bicep portions 634a and 634b. Namely, the waist size is distinguished using a pattern 632 that different from a pattern 634a/634b used to distinguish the biceps. One of ordinary skill in the art will appreciate that portions of the target visual representation 630 may be distinguished from each other in various ways, such as having different patterns, colors, shading, brightness, and/or the like.

As further illustrated in FIG. 6L, in some implementations, the electronic device 100 displays an interface 628 that provides a side-by-side comparison of a user's actual body-assessment values and target body-assessment values. Moreover, in some implementations, the electronic device 100 displays a textual indication 629 indicating which body-assessment categories satisfy the one or more body-assessment targets. Because the user's current bicep size of 12 inches satisfies the corresponding target bicep size of greater than 11 inches, the textual indication 629 indicates that the bicep size target has been satisfied. Although not illustrated, in some implementations, the electronic device 100 displays an indicator indicating one or more body-assessment targets that have not been satisfied.

Figure 7:
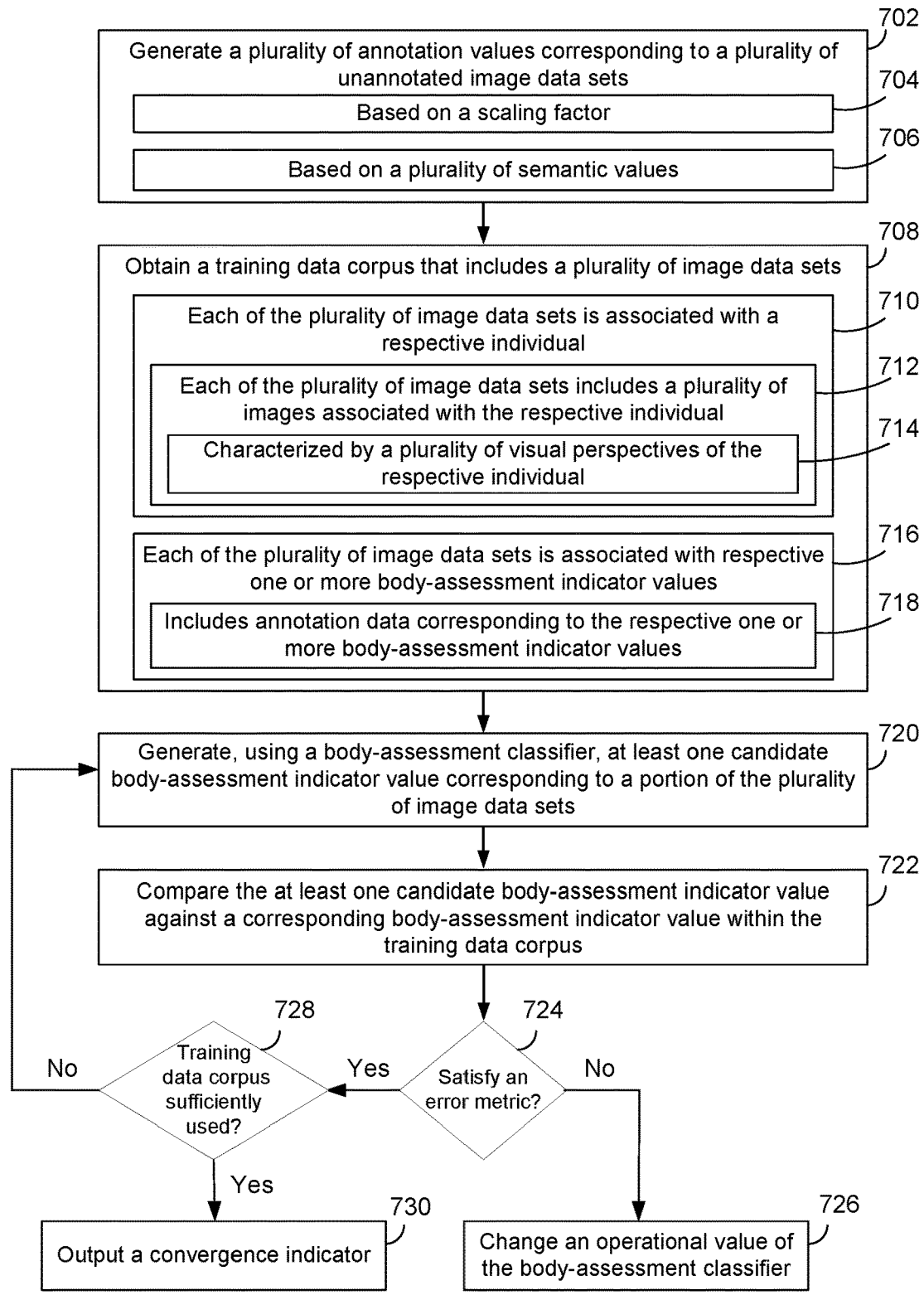
FIG. 7 is a flow diagram of a method of training a body-assessment classifier according to some implementations.

FIG. 7 is a flow diagram of a method 700 of training a body-assessment classifier according to some implementations. In various implementations, the method 700 or portions thereof are performed by a training system (e.g., the training system 211 in FIG. 2 and/or the training system 300 in FIG. 3). Briefly, the method 700 includes training a body-assessment classifier according to a comparison between at least one generated candidate body-assessment indicator value against a corresponding body-assessment indicator value included within a training data corpus.

As represented by block 702, in some implementations, the method 700 includes generating a plurality of annotation values corresponding to a plurality of unannotated image data sets. Each of the plurality of annotation values is indicative of a respective one or more body-assessment indicator values. In some implementations, with reference to FIG. 3, the training subsystem 306 obtains a plurality of unannotated image data sets and stores the plurality of unannotated image data sets within the plurality of image data sets datastore 311a. Moreover, the training subsystem 306 obtains the plurality of annotation values and stores the plurality of annotation values within the body-assessment indicator values datastore 311b.

As represented by block 704, in some implementations, the method 700 includes generating the plurality of annotation values based on a scaling factor. In some implementations, a scaling engine, such as the scaling engine 304 in FIG. 3, determines measurement values of one or more reference objects within a particular one of the plurality of unannotated image data sets and determines the scaling factor based on the measurement values. A particular annotation value corresponding to the particular one of the plurality of unannotated image data sets is based on the scaling factor.

The scaling engine 304 determines the measurement values of the one or more reference objects according to various implementations. In some implementations, the scaling engine 304 utilizes an image recognition application in order to identify the one or more reference objects and compares the one or more reference objects to known ranges of corresponding objects in order to determine corresponding measurement values. In some implementations, the scaling engine 304 utilizes instance segmentation and/or sematic segmentation in order to determine one or more dimensional values (e.g., outer area, contour) corresponding to the one or more reference objects, and determines corresponding measurement values based on the one or more dimensional values.

The scaling engine 304 determines a scaling factor based on the measurement values according to various implementations. In some implementations, the scaling engine 304 determines geographical correspondences between the one or more reference objects and uses the geographical correspondences in determining the scaling factor. For example, after determining a measurement value of an identified watch being worn by a hand of a user, the scaling engine 304 determines the angle of the user's hand and corresponding arm relative to his vertical position in determining the scaling factor. In some implementations, the scaling 304 engine utilizes an orientation of the user in an image (e.g., a top-down image versus a side-view image) in determining the scaling factor. The scaling engine 304 utilizes the scaling factor in generating a corresponding annotation value for an image.

As represented by block 706, in some implementations, the method 700 includes generating a plurality of semantic values that correspond to the plurality of unannotated image data sets. Each of the plurality of semantic values semantically characterizes the corresponding unannotated image data set. Each of the plurality of annotation values may be a function of a respective one of the plurality of semantic values. As one example, with reference to FIG. 3, the semantic engine 305 generates the plurality of semantic values that correspond to the plurality of unannotated image data sets stored in the unannotated image data sets datastore 302. For instance, the semantic engine 305 generates, from a particular unannotated image, respective semantic labels corresponding to various portions of a user's body (e.g., waist, biceps, head, legs, etc.) and utilizes the semantic labels in generating corresponding annotation values.

As represented by block 708, the method 700 includes obtaining a training data corpus that includes a plurality of image data sets. For example, with reference to FIG. 3, the training data corpus corresponds to the training data corpus 311. According to various implementations, the training data corpus includes a plurality of annotated image data sets 311a.

As represented by block 710, each of the plurality of image data sets is associated with a respective individual. For example, a first image data set is associated with a tall male bodybuilder, a second image data set is associated with a short female fitness model, a third image data set is associated with a slightly obese male, a fourth image data set is associated with a skinny female, etc. As represented by block 712, in some implementations, each of the plurality of image data sets includes a plurality of images associated with the respective individual. For example, an image data set associated with the tall made body builder includes a number of images, each corresponding to a different pose (e.g., front view bicep flex, back view bicep and back flex, side view of obliques, etc.). As represented by block 714, in some implementations, the plurality of images associated with the respective individual is characterized by a plurality of visual perspectives of the respective individual. For example, in some implementations, the plurality of images is characterized by different views of the individual at the same level, such as side-view, front-view, rear-view, and/or the like. As another example, in some implementations, plurality of images is characterized by different levels of the individual, such as vertically neutral-view; top-down view (e.g., bird's eye view), bottom-up view, side-view, and/or the like.

As represented by block 716, each of the plurality of image data sets is associated with respective one or more body-assessment indicator values. The one or more body-assessment indicator values are visually assessable. The one or more body-assessment indicator values may indicate a combination of one or more of: a visual bulk, a skin elasticity, a gender, a muscle definition, weight, height, bodyfat percentage, muscular symmetry, amount of muscle, amount of fat, ratio of muscle to fat, waist size, muscularity of particular muscles and/or muscle groups, skin information (e.g., skin elasticity), relative muscle thickness levels (e.g., upper body is more muscular than lower body), and/or the like.

As represented by block 718, in some implementations, each of the plurality of image data sets includes annotation data providing quantitative values corresponding to the respective one or more body-assessment indicator values. Annotation data includes annotation information concerning the corresponding image data set. For example, the annotation data for an image of an Olympic athlete includes "8% bodyfat," "highly muscular," "above average muscular development in lower body," etc. In some implementations, the annotation data is pre-generated from unannotated image data. In some implementations, the annotation data provides quantitative values in order to facilitate generating targeted (e.g., goal) or expected body composition information, such as 2D, 3D, stereoscopic, spatial, and/or volumetric models of the user.

The annotation data may be obtained according to variety of implementations. For example, in some implementations, the annotation data includes biometric data, provided via a user input and/or a subsystem. The biometric data includes, for example, height, weight, blood pressure, EKG information, BMI, bodyfat percentage, and/or the like. As another example, in some implementations, the annotation data includes body sensor data. The body sensor data may be obtained from a variety of sources, including but not limited to a wearable device (e.g., smartwatch, continuous blood glucose monitor (CGM)): an inertial movement unit (IMU) integrated in a device, such as a smartphone; and/or the like.

As represented by block 720, the method 700 includes generating, using a body-assessment classifier, at least one candidate body-assessment indicator value corresponding to a portion of the plurality of image data sets. A portion of the plurality of image data sets may correspond to one image data set or two or more image data sets. For example, with reference to FIG. 3, the body-assessment classifier 208 generates the at least one candidate body-assessment indicator value based on the plurality of image data sets stored in datastore 311a. The body-assessment classifier 208 provides the at least one candidate body-assessment indicator value to the training subsystem 306, which in turn stores the at least one candidate body-assessment indicator value in corresponding datastore 312.

In some implementations, the body-assessment classifier includes a number of analyzers for analyzing a corresponding image data set, such as a body composition analyzer (e.g., total amount of muscle, total amount of fat, muscle to fat ratio), body shape analyzer (e.g., height, location of fat and muscle on body—e.g., pear-shape), biometric analyzer, etc. In some implementations, a portion of the analyzers each includes a neural network, such as the neural network 500 in FIG. 5. In some implementations, the body-assessment classifier utilizes one or more of: linear regression subsystem, logistic regression subsystem, naïve Bayes subsystem, small neural network subsystem, deep learning neural network subsystem, SVM subsystem, SVM RBF subsystem, SVM linear subsystem, SVM polynomial subsystem, SVM sigmoid subsystem, random forest (Gini) subsystem, random forest (entropy) subsystem, etc.

As represented by block 722, the method 700 includes comparing the at least one candidate body-assessment indicator value against a corresponding body-assessment indicator value within the training data corpus. As represented by block 724, in some implementations, the method 700 includes determining whether or not the comparison satisfies an error metric. In some implementations, the method 700 includes aggregating some or all of the comparison results and determining whether the aggregated result satisfies the error metric. In some implementations, the error metric is satisfied when a sufficient number of the plurality of candidate body-assessment indicator values match corresponding candidate body-assessment indicator values within a threshold margin (e.g., percentage).

In response to determining that the comparison does not satisfy the error metric, the method 700 continues to a portion of the method 700 represented by block 726 ("No" path from block 724). As represented by block 726, the method 700 includes changing an operational value of the body-assessment classifier. In some implementations, changing the operation value of the body-assessment classifier corresponds to changing values of weights of a neural network, such as the neural network 500 in FIG. 5.

On the other hand, in response to determining that the comparison satisfies the error metric, the method 700) continues to a portion of the method 700 represented by block 728. As represented by block 728, the method 700 includes determining whether or not a sufficient portion of the training data corpus is utilized. In other words, whether the body-assessment classifier has processed enough image data sets. In response to determining that the sufficient portion of the training data corpus is not utilized, in some implementations, the method 700 reverts back to the portion of the method 700 represented by block 720 in order to generate additional candidate body-assessment indicator value(s). On the other hand, in response to determining that the sufficient portion of the training data corpus is utilized, the method 700 continues to a portion of the method 700 represented by block 730. As represented by block 730, the method 700 includes outputting a convergence indicator associated with the body-assessment classifier. With reference to FIG. 3, the convergence indicator 318 signals to the switch control circuit 317 to open the switch in order to prevent the operational modifier 216 from modifying operation values of the body-assessment classifier 208. In other words, the convergence indicator provides an indication to stop training body-assessment classifier 208. One of ordinary skill in the art will appreciate that the value (e.g., 0 versus 1) of the convergence indicator resulting in stopping training may differ according to different implementations.

Figure 8:
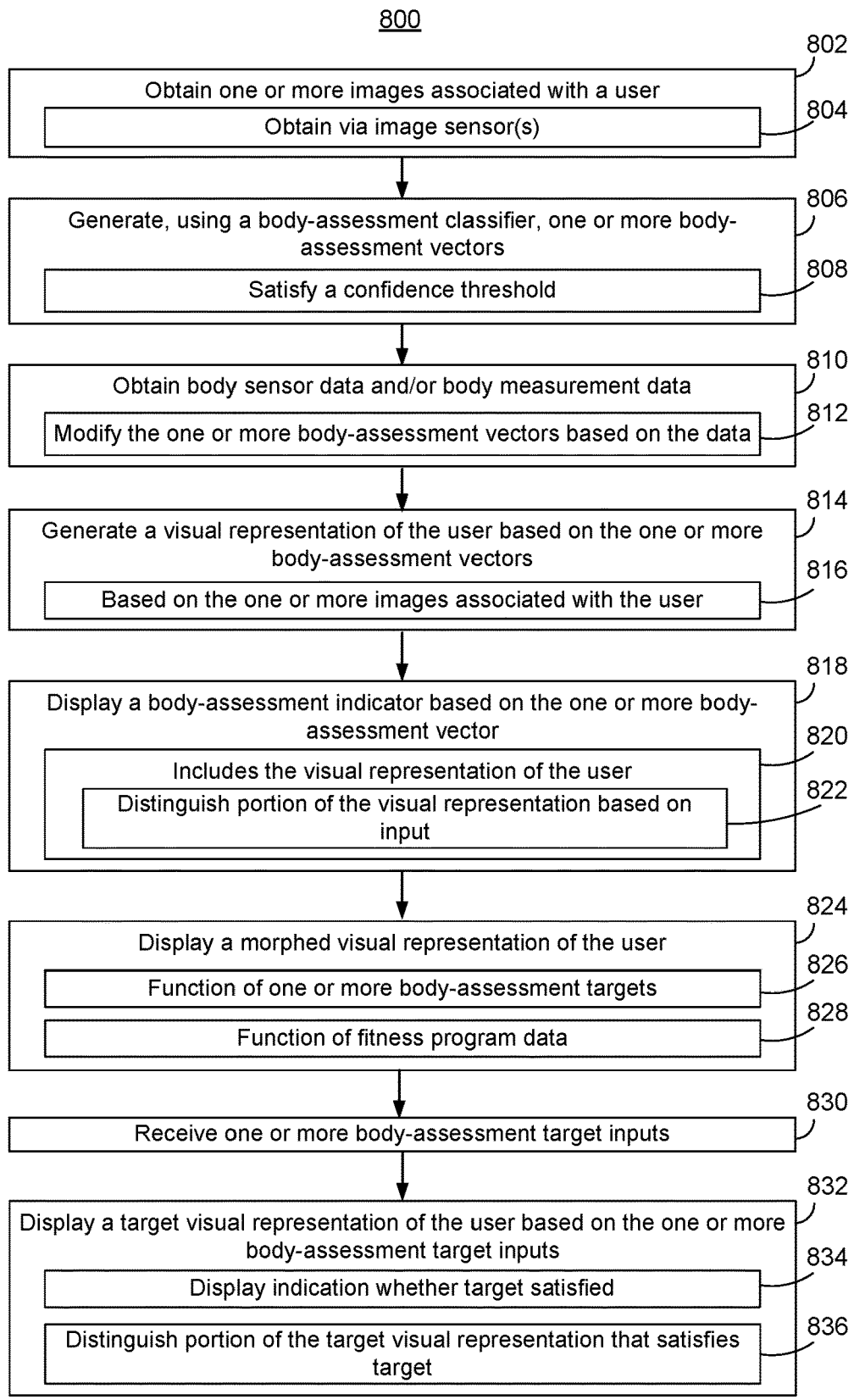
FIG. 8 is a flow diagram of a method of utilizing a body-assessment classifier for displaying body-assessment indicators according to some implementations.

FIG. 8 is a flow diagram of a method 800 of utilizing a body-assessment classifier for displaying body-assessment indicators according to some implementations. In various implementations, the method 800 or portions thereof are performed by detection (e.g., run-time) portions of a fitness system, such as portions of the fitness system 200 as described above with respect to FIG. 2. Briefly, the method 800 includes utilizing a trained body-assessment classifier in order to generate and display body-assessment indicators.

As represented by block 802, the method 800 includes obtaining one or more images associated with a user. As represented by block 804, in some implementations, a body-assessment classifier obtains the one or more images from one or more image sensors. The one or more image sensors may include a combination of a phone camera, HMD body pose cameras, tablet cameras, etc.

As represented by block 806, the method 800 includes generating, using a body-assessment classifier, one or more body-assessment vectors. Each of the one or more body-assessment vectors is a function of a particular one of the one or more images. The one or more body-assessment vectors include quantitative physique and biometric assessments associated with the user. For example, with reference to FIG. 2, the body-assessment classifier 208 obtains the one or more images from image(s) datastore 204 and generates the one or more body-assessment vectors. With reference to FIG. 4, the one or more body-assessment vectors 410-1 . . . 410-M may include a variety of quantitative physique and biometric sub-values, including but not limited to sub-values indicative of: gender, bodyfat, weight, waist size, BMI, muscle thickness, muscle density, vascularity, visibility of certain veins (e.g., visible bicep vein indicates low body fat percentage), visceral fat level (e.g., visible six pack indicates low visceral fat level), muscle to fat ratio, heart rate, EKG information, blood pressure, VO2 max, and/or the like.

As represented by block 808, in some implementations, generating the one or more body-assessment vectors includes determining that the one or more body-assessment vectors satisfy a confidence threshold. Determining that the one or more body-assessment vectors satisfy a confidence threshold may increase the accuracy of the quantitative physique and biometric assessments associated with the user. In some implementations, multiple body-assessment vectors include respective different sub-values of the same category (e.g., BMI). For example, a first BMI sub-value within a first body-assessment vector and associated with a top-down image of a user has a value of 11.2, whereas a second BMI sub-value within a second body-assessment vector and associated with a side-view image of the user has a value of 11.4. The fitness system determines that the two BMI values, 11.2 and 11.4, are sufficiently close to each other to satisfy the confidence threshold. Accordingly, the fitness system may choose one of the BMI values as the final value, or, for example, take an average of the two values (11.3). As a counter example, if the first BMI Value is 11.2 whereas the second BMI value is 14.1, the fitness system determines the confidence threshold is not satisfied because of the relatively large difference between the two values. Accordingly, the fitness system may obtain other BMI values within other body-assessment vectors for additional data points or simply discard the two BMI values and rely on other, non-BMI sub-categories (e.g., bodyfat percentage, weight).

As represented by block 810, in some implementations, the method 800 includes obtaining body sensor data (e.g., the body sensor data 218 in FIG. 2) and/or body measurement data (e.g., the body measurement data 220) in FIG. 2). In some implementations, an electronic device obtains the body sensor data from a wearable device (e.g., a smartwatch) and includes heart rate data, EKG data, blood glucose data, diet data, and/or the like. In some implementations, the electronic device obtains the body measurement data via an input including user weight, user height, user bodyfat percentage, and/or the like.

As represented by block 812, in some implementations, the method 800 includes modifying the one or more body-assessment vectors based on the body sensor data and/or the body measurement data. For example, with reference to FIG. 2, the body-assessment vector manager 222 modifies the one or more body-assessment vectors provided by the body-assessment classifier 208 based on the body sensor data 218 and/or the body measurement data 220. For example, the body-assessment vector manager 222 generates a scaling factor based on comparison between a portion of the body-assessment vector(s) and corresponding body measurement data. The body-assessment vector manager 222 uses the scaling factor to scale up or scale down other body-assessment vectors. For instance, if an electronic device obtains an input specifying measurement data indicating a user's weight is 120 pounds, and a particular body-assessment vector includes a weight sub-value indicating a weight of 140 pounds, then the body-assessment vector manager 222 determines a scaling factor of approximately 0.86 (~120/140). The body-assessment vector manager 222 scales other body-assessment vector sub-values by the scaling factor. For example, if a bodyfat percentage sub-value in a body-assessment vector is 19%, the body-assessment vector manager 222 multiplies 19% by 0.86 in order to determine a scaled bodyfat percentage sub-value of 16.34%. In some implementations, the scaling factor is based on comparison of multiple body-assessment vectors with corresponding body measurement data and/or body sensor data.

As represented by block 814, in some implementations, the method 800 includes generating a visual representation of the user based on the one or more body-assessment vectors. In some implementations, the visual representation of the user corresponds to one or more of a 2D model, a 3D model, a stereoscopic model, spatial model, and/or volumetric model. For example, with reference to FIG. 6F, the electronic device 100 generates and displays a visual representation of the user 613 based on sub-values of one or more body-assessment vectors as indicated within the interface 612. As represented by block 816, in some implementations, the visual representation of the user is based on the one or more images associated with the user. For example, a silhouette of a user within an image defines the outer boundary of the visual representation of the user. As another example, image features of a user not typically changed by participation in a fitness or diet regime, such as eye/nose shape and hair style, are used in the visual representation of the user.

As represented by block 818, the method 800 includes displaying, on a display, a body-assessment indicator that is based on the one or more body-assessment vectors. For example, with reference to FIG. 6E, the electronic device 100 displays an interface 612 that corresponds to a textual body-assessment indicator that is based on one or more body-assessment vectors. As represented by block 820, in some implementations, the body-assessment indicator includes a visual representation, such as the visual representation of the user 613 in FIG. 6F. As represented by block 822, in some implementations, the method 800 includes receiving an input corresponding to a particular portion of the visual representation of the user, and in response to receiving the input, distinguishing the particular portion of the visual representation of the user from the remainder of the visual representation of the user. In some implementations, certain body portions of the visual representation correspond to respective affordances that change display characteristics based on whether the user has selected or hovered over the certain body portions using a focus selector. For example, in response to receiving the input 614 corresponding to a bicep of the visual representation 613 in FIG. 6G, the electronic device 100 distinguishes both biceps via highlighting 615a and 615b in FIG. 6H. Moreover, as illustrated in FIG. 6H, in some implementations, in response to receiving the input 613 in FIG. 6G, the electronic device 100 displays an indicator 616 of a body-assessment vector corresponding to the particular portion of the visual representation in FIG. 6H. Namely, the indicator 616 indicates the current bicep size of the user as 12 inches.

As represented by block 824, in some implementations, the method 800 includes generating and displaying a morphed visual representation of the user by morphing the visual representation of the user. The morphed visual representation is a function of the one or more body-assessment vectors. In some implementations, a comparison between the morphed visual representation of the user and the visual representation of the user satisfies a difference threshold (e.g., are sufficiently close to each other). In some implementations, displaying the morphed visual representation of the user includes ceasing to display the visual representation of the user. In some implementations, displaying the morphed visual representation of the user is in response to receiving a user input.

As represented by block 826, in some implementations, the method 800 includes receiving one or more inputs specifying one or more body-assessment targets, wherein the morphed visual representation is a further function of the one or more body-assessment targets. The one or more body-assessment targets may correspond to goals to which a user is aspiring, such as a certain waist size, weight, etc.

As represented by block 828, in some implementations, the morphed visual representation is a further function of fitness program data. Fitness program data may include exercise program data (e.g., a particular weightlifting system, cardio, stretching, etc.) and/or diet program data (e.g., keto diet, paleo diet, macronutrient intake breakdown). An electronic device may obtain the fitness program data via an input, such as keyboard input or touch-screen input, or via a separate system or network (e.g., from the Internet). In some implementations, the fitness program is a schedule to be followed by the user, and the morphed visual representation is based on the user's level adherence to the fitness program.

As represented by block 830, in some implementations, the method 800 includes receiving one or more body-assessment target inputs specifying one or more body-assessment targets. For example, with reference to 6J, the electronic device 100 receives body-assessment target inputs 620-624 respectively specifying body-assessment targets of a waist size less than 32 inches, a bodyfat percentage less than 14%, and a bicep size greater than 11 inches.

As represented by block 832, in some implementations, the method 800 includes generating and displaying a target visual representation of the user based on the one or more body-assessment vectors and the one or more body-assessment targets. For example, the electronic device 100 displays a target visual representation of the user 630 in FIG. 6L based on the one or more body-assessment vectors that were generated based on three images specified in FIG. 6C and the body-assessment target inputs 620-624 received in FIG. 6J.

As represented by block 834, in some implementations, the method 800 includes: in accordance with a determination that the one or more body-assessment vectors satisfy the one or more body-assessment targets, displaying, on the display, a successful target indication; and in accordance with a determination that the one or more body-assessment vectors does not satisfy the one or more body-assessment targets, displaying, on the display, an unsuccessful target indication. For example, in FIG. 6L the electronic device 100 displays a successful target indication 629 indicating that the user's current bicep size of 12 inches satisfies the bicep size target of "11 inches or more" that was specified via input 624 in FIG. 6J.

As represented by block 836, in some implementations, the method 800 includes distinguishing a particular portion of the target visual representation of the user from the remainder of the target visual representation of the user. The particular portion of the target visual representation of the user is associated with a particular quantitative physique and biometric assessment that satisfies the one or more body-assessment targets. For example, body-assessment vectors indicate a bicep size of 12 inches, which satisfies the user-entered target of greater than 11 inches. Thus, the bicep(s) of the target visual representation of the user is colored green. However, the current user waist size of 35 inches is too large to satisfy the less than 32 inches target, and thus the waist of the target visual representation of the user is colored red. As another example, with reference to FIG. 6L, the electronic device 100 distinguishes the biceps from the remainder of the target visual representation of the user 630 by displaying marks 634a and 634b overlaid on the biceps, but distinguishes the waist from the remainder of the target visual representation of the user 630 by displaying a different mark 632 overlaid on the waist.

Figure 9:
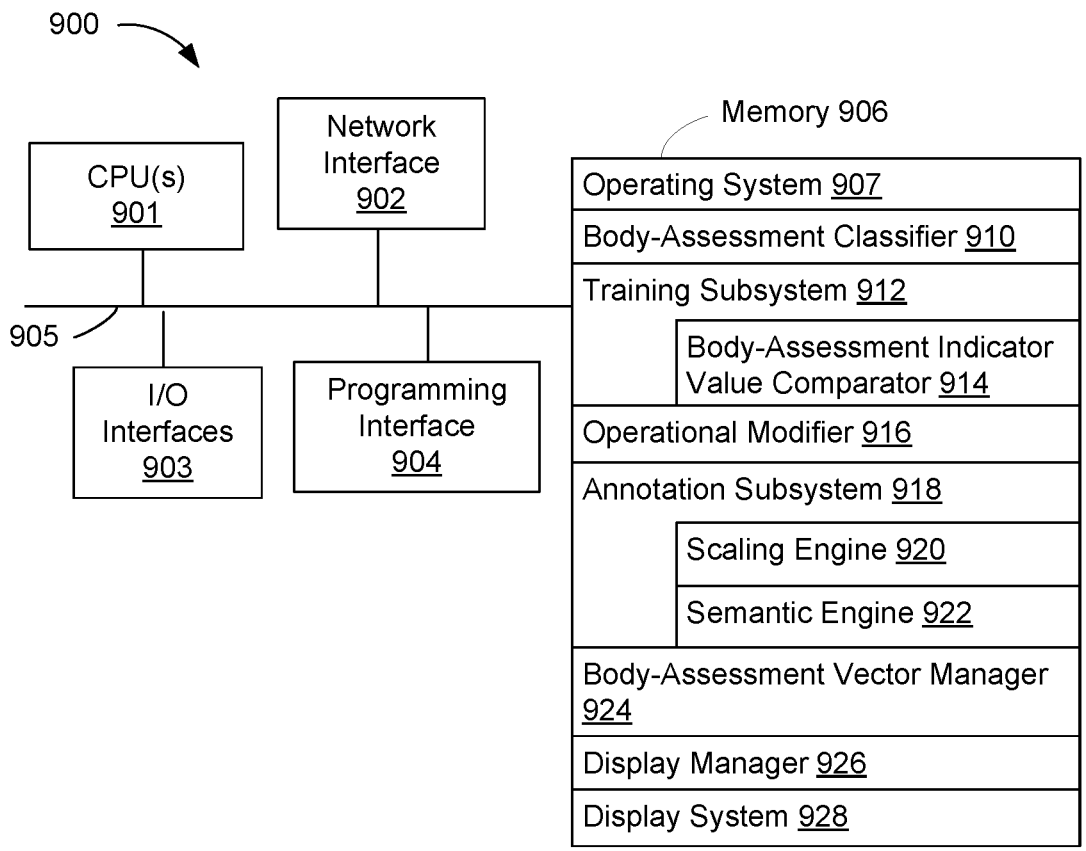
FIG. 9 is a block diagram of an example of an electronic device according to some implementations.

FIG. 9 is a block diagram of an example of an electronic device 900 according to some implementations. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations, the electronic device 900 includes one or more processing units (CPUs) 901, a network interface 902, one or more input/output (I/O) devices 903, a programming interface 904, a memory 906, and one or more communication buses 905 for interconnecting these and various other components. In some implementations, the communication buses 905 include circuitry that interconnects and controls communications between system components.

The memory 906 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 906 optionally includes one or more storage devices remotely located from the one or more CPUs 901. The memory 906 comprises a non-transitory computer readable storage medium.

In some implementations, the memory 906 or the non-transitory computer readable storage medium of the memory 906 stores the following programs, modules and data structures, or a subset thereof including an optional operating system 907, a body-assessment classifier 910 (e.g., the body-assessment classifier 208 in FIG. 2 and/or the body-assessment classifier 208 in FIG. 3), a training subsystem 912 (e.g., the training subsystem 214 in FIG. 2 and/or the training subsystem 306 in FIG. 3), a body-assessment indicator value comparator 914 (e.g., the body-assessment indicator value comparator 314 in FIG. 3), an operational modifier 916 (e.g., the operational modifier 216 in FIG. 2 and/or the operational modifier 216 in FIG. 3), an annotation subsystem 918 (e.g., the annotation subsystem 303 in FIG. 3), a scaling engine 920 (e.g., the scaling engine 304 in FIG. 3), a semantic engine 922 (e.g., the semantic engine 305 in FIG. 3), a body-assessment vector manager 924 (e.g., body-assessment vector manager 222 in FIG. 2), a display manager 926 (e.g., the display manager 223 in FIG. 2), and a display system 928 (e.g., the display system 224 in FIG. 2).

In some training implementations, the body-assessment classifier 910 is configured to generate at least one candidate body-assessment indicator value corresponding to a portion of a plurality of image data sets. In some detection (e.g., run-time) implementations, the body-assessment classifier 910 is configured to generate one or more body-assessment vectors, wherein each of the one or more body-assessment vectors is a function of a particular one of one or more images associated with a user, and wherein the one or more body-assessment vectors include quantitative physique and biometric assessments associated with the user. In some implementations, the body-assessment classifier 910 includes a neural network, such as the neural network 500 in FIG. 5.

In some implementations, the training subsystem 912 is configured to train the interaction-style classifier 910 by comparing the at least one candidate body-assessment indicator value against a corresponding body-assessment indicator value within a training data corpus. In some implementations, the body-assessment indicator value comparator 914 performs the comparison. In some implementations, based on the result of the comparison, the training subsystem 912 changes an operational value of the body-assessment classifier 910 or outputs a convergence indicator associated with the body-assessment classifier 910. In some implementations, the training subsystem 912 instructs the operational modifier 916 to change an operational value of the body-assessment classifier 910.

In some implementations, the annotation subsystem 918 generates annotation values corresponding to unannotated image data sets and provides the annotation values and the unannotated image data sets to the training subsystem 912. In turn, the training subsystem 912 may utilize the annotation values and the unannotated image data sets in training the body-assessment classifier 910. In some implementations, the annotation subsystem 918 utilizes a scaling engine 920) and/or a semantic engine 922 in generating the annotation values.

In some implementations, based on body sensor data and/or body measurement data, the body-assessment vector manager 924 modifies the one or more body-assessment vectors generated by the body-assessment classifier 910.

In some implementations, the display manager 926 obtains one or more modified and/or unmodified body-assessment vectors and displays, via the display system 928, a body-assessment indicator that is based on the one or more body-assessment vectors. In some implementations, a body-assessment indicator includes a visual representation of a user. In some implementations, the display manager 926 utilizes body-assessment target input(s) in order to display a modified visual representation of a user and/or generate and display a target visual representation of the user.

Moreover, FIG. 9) is intended more as a functional description of the various features which are present in a particular implementation as opposed to a structural schematic of the implementations described herein. As recognized by those of ordinary skill in the art, items shown separately could be combined and some items could be separated. For example, some functional modules shown separately in FIG. 9 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be implemented in such program instructions, although some or all of the disclosed functions may alternatively be implemented in application-specific circuitry (e.g., ASICs or FPGAs or GP-GPUs) of the computer system. Where the computer system includes multiple computing devices, these devices may be co-located or not co-located. The results of the disclosed methods and tasks may be persistently stored by transforming physical storage devices, such as solid-state memory chips and/or magnetic disks, into a different state.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various implementations described above can be combined to provide further implementations. Accordingly, the novel methods and systems described herein may be implemented in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method comprising:
   at an electronic device including one or more processors, a non-transitory memory, and a display:
   obtaining one or more images associated with a user, wherein each of the one or more images represents a different orientation of the user;
   providing the one or more images to a body-assessment classifier to generate one or more body-assessment vectors, wherein each of the one or more body-assessment vectors associated with a respective image represents quantitative physique and biometric assessments associated with the user, wherein the body-assessment classifier is trained using images of individuals from different views and annotation values representing a plurality of quantitative physique and biometric assessments associated with the individuals in order to produce body-assessment vectors based on image data;
   displaying, on the display, a body-assessment indicator that is based on the one or more body-assessment vectors;
   receiving one or more body-assessment target inputs specifying one or more body-assessment targets, wherein the one or more body-assessment targets include a first target dimension for a first body part and a second target dimension for a second body part;
   generating a target visual representation of the user based on the one or more body-assessment vectors and the one or more body-assessment targets;
   displaying, on the display, the target visual representation of the user;
   overlaying, on a first portion of the target visual representation that corresponds to the first body part, a first indicator to indicate that the first body part satisfies the first target dimension for the first body part; and
   overlaying, on a second portion of the target visual representation that corresponds to the second body part, a second indicator to indicate that the second body part does not satisfy the second target dimension for the second body part.

2. The method of claim 1, further comprising:
   obtaining body sensor data associated with the user; and
   modifying the one or more body-assessment vectors based on the body sensor data.

3. The method of claim 2, wherein the electronic device obtains the body sensor data from a wearable device.

4. The method of claim 1, further comprising:
   receiving, via one or more input devices, an input providing body measurement data associated with the user; and
   modifying the one or more body-assessment vectors based on the body measurement data provided by the input.

5. The method of claim 1, further comprising:
   generating a visual representation of the user based on the one or more body-assessment vectors; and
   wherein the body-assessment indicator includes the visual representation of the user.

6. The method of claim 5, wherein the visual representation of the user is based on the one or more images associated with the user.

7. The method of claim 5, further comprising:
   receiving an input corresponding to a particular portion of the visual representation of the user; and
   in response to receiving the input, distinguishing the particular portion of the visual representation of the user from remainder of the visual representation of the user.

8. The method of claim 5, further comprising:
   generating a morphed visual representation of the user by morphing the visual representation of the user, wherein the morphed visual representation is a function of the one or more body-assessment vectors; and
   displaying, on the display, the morphed visual representation of the user.

9. The method of claim 8, further comprising:
   receiving one or more inputs specifying one or more body-assessment targets;
   wherein the morphed visual representation is a further function of the one or more body-assessment targets.

10. The method of claim 8, wherein the morphed visual representation is a further function of fitness program data.

11. The method of claim 1, wherein providing the one or more images to the body-assessment classifier to generate the one or more body-assessment vectors includes determining that the one or more body-assessment vectors satisfy a confidence threshold.

12. The method of claim 1, wherein obtaining the one or more images associated with the user includes obtaining, via one or more image sensors, the one or more images associated with the user.

13. The method of claim 1, wherein the one or more images includes a first image that represents a first orientation of the user and a second image that represents a second orientation of the user;
wherein the one or more body-assessment vectors includes a first body-assessment vector associated with the first image of the user and a second body-assessment vector associated with second image of the user;
wherein the first body-assessment vector includes a first set of quantitative physique and biometric assessments associated with the user and the second body-assessment vector includes a second set of quantitative physique and biometric assessments associated with the user; and
wherein the body-assessment indicator is based on a function of the first set of quantitative physique and biometric assessments included in the first body-assessment vector and the second set of quantitative physique and biometric assessments included in the second body-assessment vector.

14. The method of claim 13, wherein the body-assessment indicator is based on an average of the first set of quantitative physique and biometric assessments included in the first body-assessment vector and the second set of quantitative physique and biometric assessments included in the second body-assessment vector.

15. An electronic device comprising:
one or more processors;
a non-transitory memory;
a display; and
one or more programs, wherein the one or more programs are stored in the non-transitory memory and configured to be executed by the one or more processors, the one or more programs including instructions for:
obtaining one or more images associated with a user, wherein each of the one or more images represents a different orientation of the user;
providing the one or more images to a body-assessment classifier to generate one or more body-assessment vectors, wherein each of the one or more body-assessment vectors associated with a respective image represents quantitative physique and biometric assessments associated with the user, wherein the body-assessment classifier is trained using images of individuals from different views and annotation values representing a plurality of quantitative physique and biometric assessments associated with the individuals in order to produce body-assessment vectors based on image data;
displaying, on the display, a body-assessment indicator that is based on the one or more body-assessment vectors;
receiving one or more body-assessment target inputs specifying one or more body-assessment targets, wherein the one or more body-assessment targets include a first target dimension for a first body part and a second target dimension for a second body part;
generating a target visual representation of the user based on the one or more body-assessment vectors and the one or more body-assessment targets;
displaying, on the display, the target visual representation of the user;
overlaying, on a first portion of the target visual representation that corresponds to the first body part, a first indicator to indicate that the first body part satisfies the first target dimension for the first body part; and
overlaying, on a second portion of the target visual representation that corresponds to the second body part, a second indicator to indicate that the second body part does not satisfy the second target dimension for the second body part.

16. The electronic device of claim 15, wherein the one or more programs include instructions for:
generating a visual representation of the user based on the one or more body-assessment vectors; and
wherein the body-assessment indicator includes the visual representation of the user.

17. The electronic device of claim 16, wherein the one or more programs include instructions for:
generating a morphed visual representation of the user by morphing the visual representation of the user, wherein the morphed visual representation is a function of the one or more body-assessment vectors; and
displaying, on the display, the morphed visual representation of the user.

18. The electronic device of claim 17, wherein the one or more programs include instructions for:
receiving one or more inputs specifying one or more body-assessment targets;
wherein the morphed visual representation is a further function of the one or more body-assessment targets.

19. A non-transitory computer readable storage medium storing one or more programs, the one or more programs comprising instructions, which, when executed by an electronic device with one or more processors and a display, cause the electronic device to:
obtain one or more images associated with a user, wherein each of the one or more images represents a different orientation of the user;
provide the one or more images to a body-assessment classifier to generate one or more body-assessment vectors, wherein each of the one or more body-assessment vectors associated with a respective image represents quantitative physique and biometric assessments associated with the user, wherein the body-assessment classifier is trained using images of individuals from different views and annotation values representing a plurality of quantitative physique and biometric assessments associated with the individuals in order to produce body-assessment vectors based on image data;
display, on the display, a body-assessment indicator that is based on the one or more body-assessment vectors;
receive one or more body-assessment target inputs specifying one or more body-assessment targets, wherein the one or more body-assessment targets include a first target dimension for a first body part and a second target dimension for a second body part;
generate a target visual representation of the user based on the one or more body-assessment vectors and the one or more body-assessment targets;
display, on the display, the target visual representation of the user;

overlay, on a first portion of the target visual representation that corresponds to the first body part, a first indicator to indicate that the first body part satisfies the first target dimension for the first body part; and overlay, on a second portion of the target visual representation that corresponds to the second body part, a second indicator to indicate that the second body part does not satisfy the second target dimension for the second body part.

* * * * *